US010605915B2

(12) United States Patent
Kiyose et al.

(10) Patent No.: US 10,605,915 B2
(45) Date of Patent: Mar. 31, 2020

(54) ULTRASONIC DEVICE, ULTRASONIC MODULE, ELECTRONIC APPARATUS, AND ULTRASONIC MEASUREMENT APPARATUS

(71) Applicant: Seiko Epson Corporation, Tokyo (JP)

(72) Inventors: Kanechika Kiyose, Matsumoto (JP); Hikaru Iwai, Ina (JP)

(73) Assignee: Seiko Epson Corporation (JP)

( * ) Notice: Subject to any disclaimer, the term of this patent is extended or adjusted under 35 U.S.C. 154(b) by 518 days.

(21) Appl. No.: 15/219,623

(22) Filed: Jul. 26, 2016

(65) Prior Publication Data

US 2017/0031024 A1    Feb. 2, 2017

(30) Foreign Application Priority Data

Jul. 30, 2015 (JP) .................. 2015-150418

(51) Int. Cl.
*B06B 1/06* (2006.01)
*G01S 15/89* (2006.01)
(Continued)

(52) U.S. Cl.
CPC ........ *G01S 15/8915* (2013.01); *A61B 8/4281* (2013.01); *A61B 8/4444* (2013.01);
(Continued)

(58) Field of Classification Search
None
See application file for complete search history.

(56) References Cited

U.S. PATENT DOCUMENTS 5,834,877 A * 11/1998 Buisker ................. B06B 1/0622
310/322
7,458,967 B2 * 12/2008 Appling ................. A61B 18/24
600/101
(Continued)

FOREIGN PATENT DOCUMENTS

JP   58-078652 A   5/1983
JP   H11-198369 A   7/1999
(Continued)

OTHER PUBLICATIONS

Huang, Yongli, et al. "Capacitive micromachined ultrasonic transducers with piston-shaped membranes: Fabrication and experimental characterization." IEEE transactions on ultrasonics, ferroelectrics, and frequency control 56.1 (2009): 136-145. (Year: 2009).*
(Continued)

*Primary Examiner* — Hovhannes Baghdasaryan
*Assistant Examiner* — Jonathan D Armstrong
(74) *Attorney, Agent, or Firm* — Harness, Dickey & Pierce, P.L.C.

(57) ABSTRACT

An ultrasonic device includes an element substrate provided with an ultrasonic transducer array having a plurality of ultrasonic transducers arranged in an array, and having a first surface and a second surface located on an opposite side to the first surface, a terminal part disposed on the first surface of the element substrate, and outside the ultrasonic transducer array in a planar view viewed from a normal direction of the first surface, and electrically connected to the ultrasonic transducers, and a reinforcing plate disposed on the second surface of the element substrate in an area overlapping the terminal part in the planar view, and higher in bending rigidity than the element substrate.

1 Claim, 11 Drawing Sheets

(51) Int. Cl.
*A61B 8/00* (2006.01)
*G01S 7/52* (2006.01)
(52) U.S. Cl.
CPC .......... *A61B 8/4494* (2013.01); *B06B 1/0629* (2013.01); *G01S 7/52077* (2013.01); *G01S 7/52079* (2013.01)

(56) References Cited

U.S. PATENT DOCUMENTS

| | | | | |
|---|---|---|---|---|
| 8,887,733 | B2* | 11/2014 | Appling | A61B 18/24 |
| | | | | 128/898 |
| 9,079,220 | B2* | 7/2015 | Nakamura | B06B 1/0622 |
| 9,089,872 | B2* | 7/2015 | Nakamura | B06B 1/0207 |
| 9,554,775 | B2* | 1/2017 | Nakamura | B06B 1/0622 |
| 10,040,098 | B2* | 8/2018 | Nakamura | B06B 1/0622 |
| 2004/0100163 | A1* | 5/2004 | Baumgartner | B06B 1/0622 |
| | | | | 310/334 |
| 2005/0107703 | A1* | 5/2005 | Bullis | A61B 8/0825 |
| | | | | 600/442 |
| 2006/0085049 | A1* | 4/2006 | Cory | A61B 5/0536 |
| | | | | 607/48 |
| 2009/0301200 | A1* | 12/2009 | Tanaka | B06B 1/0292 |
| | | | | 73/603 |
| 2013/0258802 | A1* | 10/2013 | Nakamura | B06B 1/0207 |
| | | | | 367/7 |
| 2013/0258803 | A1* | 10/2013 | Nakamura | B06B 1/0622 |
| | | | | 367/7 |
| 2014/0276053 | A1* | 9/2014 | Sanghvi | A61B 8/4494 |
| | | | | 600/439 |
| 2014/0292941 | A1 | 10/2014 | Kobayashi et al. | |
| 2017/0020484 | A1* | 1/2017 | Kiyose | A61B 8/4494 |
| 2017/0031024 | A1* | 2/2017 | Kiyose | G01S 15/8915 |
| 2017/0119349 | A1* | 5/2017 | Miyazawa | A61B 8/4494 |
| 2017/0156691 | A1* | 6/2017 | Cabrera-Munoz | A61B 8/12 |
| 2017/0156695 | A1* | 6/2017 | Nakamura | A61B 8/14 |
| 2017/0209121 | A1* | 7/2017 | Davis, Sr. | A61B 8/14 |
| 2017/0244022 | A1* | 8/2017 | Kojima | A61B 8/14 |

FOREIGN PATENT DOCUMENTS

| | | |
|---|---|---|
| JP | 2007-276121 A | 10/2007 |
| JP | 2011-259274 A | 12/2011 |
| JP | 2014-194993 A | 10/2014 |
| JP | 2015-160104 A | 9/2015 |

OTHER PUBLICATIONS

Sato, M., et al. "Capacitive micromachined ultrasonic transducers with novel membrane design.", Procedia Chemistry;1.1 (2009): 389-392. (Year: 2009).*

* cited by examiner

ULTRASONIC DEVICE, ULTRASONIC MODULE, ELECTRONIC APPARATUS, AND ULTRASONIC MEASUREMENT APPARATUS

BACKGROUND

1. Technical Field

The present invention relates to an ultrasonic device, an ultrasonic module, an electronic apparatus, and an ultrasonic measurement apparatus.

2. Related Art

In the past, there has been known an ultrasonic device provided with a movable film, and vibrating the movable film to thereby output an ultrasonic wave (see, e.g., JP-A-2011-259274 (Document 1)).

An ultrasonic transmission/reception section of an ultrasonic probe of Document 1 is provided with a support member, a diaphragm (the movable film) disposed on an opposite side to the radiation direction of the ultrasonic wave in the support member, and a sealing member disposed on the opposite side of the support member and for sealing the diaphragm. Further, on the surface on the opposite side of the support member, there is disposed a terminal part electrically connected to an electrode layer constituting the diaphragm, and the terminal part is connected to one end part of a through electrode provided to the sealing member via a solder bump. According to this configuration, by connecting the other end part of the through electrode to a wiring board, the ultrasonic transmission/reception section can be mounted on the wiring board.

Incidentally, as another method of mounting the ultrasonic transmission/reception section on the wiring board, it is possible to adopt a method using, for example, flexible printed circuits (FPC).

In this method, the sealing member is provided with a through hole for exposing the terminal part disposed on the support member, the FPC is inserted in the through hole, and the electrode of the FPC and the terminal part are connected to each other. Further, by the other electrodes of the FPC located outside the through hole being connected to the wiring board, the ultrasonic transmission/reception section can be mounted on the wiring board. In this case, in order to protect the terminal part exposed from the sealing member, the terminal part is covered with a protective member made of resin or the like.

However, according to this configuration, the protective member is softened by, for example, the heat applied when mounting the ultrasonic transmission/reception section on the wiring board, and is then contracted when being hardened. Further, the stress due to the contraction is applied to the support member. In the ultrasonic transducer shaped like a thin film, since the support member small in thickness is used, if the stress is applied to the support member, the support member is warped.

SUMMARY

An advantage of some aspects of the invention is to provide an ultrasonic device, an ultrasonic module, an electronic apparatus, and an ultrasonic measurement apparatus each capable of suppressing the warpage.

An ultrasonic device of an application example according to the invention includes an element substrate provided with an ultrasonic transducer array having a plurality of ultrasonic transducers arranged in an array, and having a first surface and a second surface located on an opposite side to the first surface, at least one terminal part disposed on the first surface of the element substrate, and outside the ultrasonic transducer array in a planar view viewed from a normal direction of the first surface, and electrically connected to the ultrasonic transducers, a reinforcing plate, which is disposed on the second surface of the element substrate and in an area overlapping the terminal part in the planar view, and is higher in bending rigidity than the element substrate.

The ultrasonic device is mounted on the wiring board using, for example, FPC. In this case, the terminal part is connected to the electrode of the FPC, and is further covered with the protective member such as resin. Further, by connecting other electrodes of the FPC to the wiring board, the ultrasonic device is mounted on the wiring board. On this occasion, the protective member is softened by, for example, the heat applied when mounting, and is then contracted when being hardened. Further, the stress due to the contraction is applied to the element substrate. As the method of mounting the ultrasonic device on the wiring board, there can be cited, for example, a method of connecting the terminal part disposed on the element substrate directly to the wiring board using solder besides the above. However, even in this case, there is a possibility that the stress due to the contraction of the solder is applied to the element substrate, or the element substrate itself contracts due to the heat generated when making the solder in the melted state have contact with the terminal part.

Here, in this application example, as described above, the reinforcing plate higher in bending rigidity (harder) than the element substrate is disposed on the second surface of the element substrate and in the area overlapping the terminal part in the planar view described above. According to this configuration, in the case of, for example, connecting the FPC to the terminal part of the element substrate, and then covering the connection part with the protective member, even if a stress due to the contraction of the protective member is applied to the element substrate, since the area corresponding to the terminal part of the element substrate is reinforced by the reinforcing plate, a warp of the element substrate can be suppressed.

In the ultrasonic device according to the application example, it is preferable that the ultrasonic device further includes a sealing plate disposed on the first surface side of the element substrate, the sealing plate is provided with at least one through hole penetrating the sealing plate in a thickness direction disposed in the area overlapping the terminal part in the planar view, and the reinforcing plate is disposed in the area overlapping the through hole in the planar view.

By disposing the through hole in the sealing plate, the terminal part disposed on the element substrate is exposed from the through hole. Therefore, by inserting, for example, the FPC in the through hole, connecting the electrode of the FPC and the terminal part to each other, and connecting the other electrode of the FPC and the wiring board to each other, the ultrasonic device can be mounted on the wiring board. On this occasion, even in the case of filling the through hole of the sealing plate with the protective member such as resin for protecting the connection part between the FPC and the terminal part, since the reinforcing plate is disposed in the area overlapping the through hole, the stress due to the contraction of the protective member can be relaxed, and the warp of the element substrate can be suppressed. Further, by filling the through hole with the protective member, the protective member is prevented from spreading to an area where the reinforcing plate is not disposed. In other words, it becomes possible to dispose the protective member in the part which is increased in the bending rigidity to the stress by the reinforcing plate, and the warp of the element substrate can also be suppressed in this regard.

In the ultrasonic device according to the application example, it is preferable that the element substrate has a reference thickness part having a predetermined reference thickness dimension, and a thin part smaller in thickness dimension than the reference thickness part, and a region, in which the reinforcing plate is disposed, in the element substrate corresponds to the thin part, and the second surface in the region is located closer to the first surface than the second surface in the reference thickness part.

According to the application example with this configuration, the reinforcing plate is disposed in the thin part small in the thickness dimension of the element substrate, and the second surface of the thin part on which the reinforcing plate is disposed is located closer to the first surface than the second surface in the reference thickness part. In other words, the area (hereinafter referred to as a reinforced area) on which the reinforcing plate is disposed of the element substrate has a recessed shape or a step shape toward the first surface. Therefore, by disposing the reinforcing plate in the part having the recessed shape or the step shape described above, the total thickness dimension of the element substrate and the reinforcing plate can be decreased compared to the case of, for example, disposing the reinforcing plate in the area having the same thickness dimension as the reference thickness part, and thus height reduction of the ultrasonic device can be facilitated.

In the ultrasonic device according to the application example, it is preferable that the element substrate is provided with opening parts corresponding respectively to the ultrasonic transducers, and vibrating parts respectively closing the first surface side of the opening parts, and the second surface of the region, in which the reinforcing plate is disposed, of the element substrate is coplanar with a surface of the vibrating part facing the opening part.

In the application example with this configuration, the element substrate is provided with opening parts corresponding respectively to the ultrasonic transducers, and vibrating parts respectively closing the first surface side of the opening parts. According to this configuration, by driving the ultrasonic transducers to vibrate the vibrating parts, it is possible to emit the ultrasonic wave, and further, by detecting the deformation of the ultrasonic transducers due to the vibration of the vibrating part, it is possible to receive the ultrasonic wave.

Further, the opening parts and the reinforced area in the element substrate can be formed by performing etching on, for example, a flat substrate.

In this case, according to the application example, since it is sufficient to performing the etching with the same depth on the opening parts and the reinforced area, the opening parts and the reinforced area can easily be formed compared to the case of performing etching with respective depths different from each other.

In the ultrasonic device according to the application example, it is preferable that the ultrasonic transducer array has an array structure in which the plurality of ultrasonic transducers arranged along a first direction and connected to each other by a same signal line constitutes an ultrasonic transducer group, and a plurality of ultrasonic transducer groups is arranged along a second direction crossing the first direction, the terminal part is disposed on at least one end side out of the both ends in the first direction of each of the ultrasonic transducer groups, and the reinforcing plate is disposed along the second direction on the at least one end side out of the both ends in the first direction of the ultrasonic transducer array.

In this application example, the ultrasonic transducer group is formed of the ultrasonic transducers arranged along the first direction, and it is possible to make one ultrasonic transducer group function as one channel in the ultrasonic transmission/reception operation. By arranging the plurality of such ultrasonic transducer groups along the second direction, the one-dimensional ultrasonic array is formed in the application example. In this case, simplification of the wiring can be achieved, and the miniaturization of the ultrasonic device can be achieved compared to the case of individually providing signal line to each of the ultrasonic transducers arranged in a one-dimensional array. On this occasion, the position of the terminal part is set to at least one end side out of the both ends in the first direction, and the terminal parts corresponding to the respective ultrasonic transducer groups are arranged along the second direction. Further, by disposing the reinforcing plate longitudinal along the second direction on the at least one end side out of the both ends in the first direction in the ultrasonic transducer array, it is possible to easily cover the region corresponding to the terminal parts with the reinforcing plate. In other words, there is no need to dispose the reinforcing plates corresponding respectively to the terminal parts, and the reinforcing plate can be disposed throughout the plurality of terminal parts arranged in the second direction, and thus simplification of the configuration can be achieved.

In the ultrasonic device according to the application example, it is preferable that the reinforcing plate is formed to have a frame-like shape, and surrounds the ultrasonic transducer array in the planar view.

According to the application example with this configuration, in the case in which, for example, the ultrasonic transducer array has the array structure described above, since the element substrate can more firmly be reinforced compared to the case in which the reinforcing plates are disposed only on the both ends in the first direction of the ultrasonic transducer array, the warp of the element substrate can further be suppressed.

In the ultrasonic device according to the application example, it is preferable that the ultrasonic transducer array has an array structure in which the plurality of ultrasonic transducers arranged along a first direction and connected to each other by a same signal line constitutes an ultrasonic transducer group, and a plurality of ultrasonic transducer groups is arranged along a second direction crossing the first direction, the element substrate is provided with a plurality of evaluating ultrasonic transducers arranged along the first direction disposed on both sides in the second direction of the ultrasonic transducer array, the terminal parts are respectively disposed on both ends in the first direction of each of the ultrasonic transducer groups, and the reinforcing plate is provided with terminal region reinforcing parts disposed along the second direction respectively on both ends in the first direction in the ultrasonic transducer array, and evaluation element region reinforcing parts disposed along the first direction respectively on both ends in the second direction in the ultrasonic transducer array and in areas overlapping the plurality of evaluating ultrasonic transducers in the planar view.

It should be noted that the evaluating ultrasonic transducer is an element used for, for example, the product inspection, and is not used for the normal transmission/reception of the ultrasonic waves since the reinforcing plate is disposed after the completion of the inspection.

According to the application example with this configuration, the positions of the terminal parts are set to the both ends in the first direction of each of the ultrasonic transducer groups, and the terminal parts corresponding respectively to the ultrasonic transducer groups are arranged along the second direction. Further, by disposing the reinforcing plates longitudinal along the second direction on the both ends in the first direction in the ultrasonic transducer array, it is possible to easily cover the region corresponding to the terminal parts with the reinforcing plate.

Further, by disposing the evaluation element region reinforcing parts longitudinal along the first direction on the both ends in the second direction in the ultrasonic transducer array, it is possible to easily cover the regions of the element substrate corresponding to the evaluating ultrasonic transducers with the reinforcing plate. Further, by covering the regions with the reinforcing plate, it is possible to inhibit a crack or the like from occurring in the element substrate in the regions in the case in which, for example, an impact is applied to the ultrasonic device, and thus, breakage of the evaluating ultrasonic transducers can be inhibited.

In the ultrasonic device according to the application example, it is preferable that the element substrate is provided with opening parts corresponding respectively to the ultrasonic transducers, and vibrating parts respectively closing the first surface side of the opening parts, and a surface, which is not bonded to the element substrate, of the reinforcing plate is one of coplanar with an opening surface of each of the opening parts, and located in a direction of getting away from the first surface with respect to the opening surface.

Normally, the ultrasonic device is provided with an acoustic matching layer, which relaxes the difference in acoustic impedance between the ultrasonic transducer array and an object as the transmission destination (transmission (reflection) source of the ultrasonic wave in the case of the ultrasonic reception) of the ultrasonic wave, disposed in the transmission or reception direction in the ultrasonic transducer array. Here, if the air layer high in acoustic impedance intervenes between the acoustic matching layer and the ultrasonic transducer array, the ultrasonic wave is reflected by the boundary therebetween. Therefore, the opening parts are filled with the acoustic matching layer so that the opening parts in the element substrate are completely filled with the acoustic matching layer.

On this occasion, in the application example with this configuration, the surface (the reinforcing plate surface) of the reinforcing plate not bonded to the element substrate is located on the same plane as the opening surface in the opening parts, or located in the direction of getting away from the first surface with respect to the opening surface. Therefore, when forming the acoustic matching layer, it becomes possible to form the acoustic matching layer having the uniform thickness dimension with reference to the reinforcing plate surface by filling the opening parts with the material (e.g., silicone) for forming the acoustic matching layer, and then removing the surplus part of the material along the reinforcing plate surface. Further, in the case of forming the reinforcing plate so as to have a frame-like shape, it is also possible to stem the material with the reinforcing plate.

In the ultrasonic device according to the application example, it is preferable that the reinforcing plate is provided with a terminal region reinforcing part disposed in an area overlapping the terminal part, and an inter-element region reinforcing part disposed between the ultrasonic transducers in the planar view.

According to the application example with this configuration, since the element substrate can more firmly be reinforced compared to the case in which the reinforcing plate is not disposed in the part overlapping the ultrasonic transducer array in the planar view described above in the element substrate, the warp of the element substrate can further be suppressed. Further, the cross talk between the ultrasonic transducers can also be reduced.

An ultrasonic module according to an application example of the invention includes an element substrate provided with an ultrasonic transducer array having a plurality of ultrasonic transducers arranged in an array, and having a first surface and a second surface located on an opposite side to the first surface, at least one terminal part disposed on the first surface of the element substrate, and outside the ultrasonic transducer array in a planar view viewed from a normal direction of the first surface, and electrically connected to the ultrasonic transducers, a reinforcing plate, which is disposed on the second surface of the element substrate and in an area overlapping the terminal part in the planar view, and is higher in bending rigidity than the element substrate, a connection member connected to the terminal part, a protective member adapted to cover the terminal part, and a wiring board connected to the connection member.

Since the ultrasonic module according to this application example is provided with the reinforcing plate higher in bending rigidity than the element substrate disposed on the second surface of the element substrate and in the area overlapping the terminal part in the planar view similarly to the ultrasonic device described above, in the case in which the stress due to the contraction of, for example, the protective member is applied to the element substrate, the warp of the element substrate can be suppressed.

An electronic apparatus according to an application example of the invention includes an element substrate provided with an ultrasonic transducer array having a plurality of ultrasonic transducers arranged in an array, and having a first surface and a second surface located on an opposite side to the first surface, at least one terminal part disposed on the first surface of the element substrate, and outside the ultrasonic transducer array in a planar view viewed from a normal direction of the first surface, and electrically connected to the ultrasonic transducers, a reinforcing plate, which is disposed on the second surface of the element substrate and in an area overlapping the terminal part in the planar view, and is higher in bending rigidity than the element substrate, a connection member connected to the terminal part, a protective member adapted to cover the terminal part, a wiring board connected to the connection member, and a control section adapted to control the ultrasonic transducers.

Since the electronic apparatus according to this application example is provided with the reinforcing plate higher in bending rigidity than the element substrate disposed on the second surface of the element substrate and in the area overlapping the terminal part in the planar view similarly to the ultrasonic device and the ultrasonic module described above, in the case in which the stress due to the contraction of, for example, the protective member is applied to the element substrate, the warp of the element substrate can be suppressed.

Therefore, in the electronic apparatus incorporating such an ultrasonic device or such an ultrasonic module, the functions and the advantages described above can be obtained, and accurate transmission/reception of the ultrasonic wave can be performed.

An ultrasonic measurement apparatus according to an application example of the invention includes an element substrate provided with an ultrasonic transducer array having a plurality of ultrasonic transducers arranged in an array, and having a first surface and a second surface located on an opposite side to the first surface, at least one terminal part disposed on the first surface of the element substrate, and outside the ultrasonic transducer array in a planar view viewed from a normal direction of the first surface, and electrically connected to the ultrasonic transducers, a reinforcing plate, which is disposed on the second surface of the element substrate and in an area overlapping the terminal part in the planar view, and is higher in bending rigidity than the element substrate, a connection member connected to the terminal part, a protective member adapted to cover the terminal part, a wiring board connected to the connection member, and a measurement control section adapted to control transmission of an ultrasonic wave from the ultrasonic transducer array and reception of the ultrasonic wave reflected to measure a measurement target based on transmission/reception timing of the ultrasonic wave.

Since the ultrasonic measurement apparatus according to this application example is provided with the reinforcing plate higher in bending rigidity than the element substrate disposed on the second surface of the element substrate and in the area overlapping the terminal part in the planar view similarly to the ultrasonic device and the ultrasonic module described above, in the case in which the stress due to the contraction of, for example, the protective member is applied to the element substrate, the warp of the element substrate can be suppressed.

Therefore, in the ultrasonic measurement apparatus incorporating such an ultrasonic device or such an ultrasonic module, the functions and the advantages described above can be obtained, and accurate transmission/reception of the ultrasonic wave can be performed, and further, an accurate measurement process of the object using the ultrasonic wave can be performed.

BRIEF DESCRIPTION OF THE DRAWINGS

The invention will be described with reference to the accompanying drawings, wherein like numbers reference like elements.

DESCRIPTION OF EXEMPLARY EMBODIMENTS

An ultrasonic measurement apparatus as an electronic apparatus of an embodiment according to the invention will hereinafter be described with reference to the accompanying drawings.

First Embodiment

Configuration of Ultrasonic Measurement Apparatus 1

Figure 1:
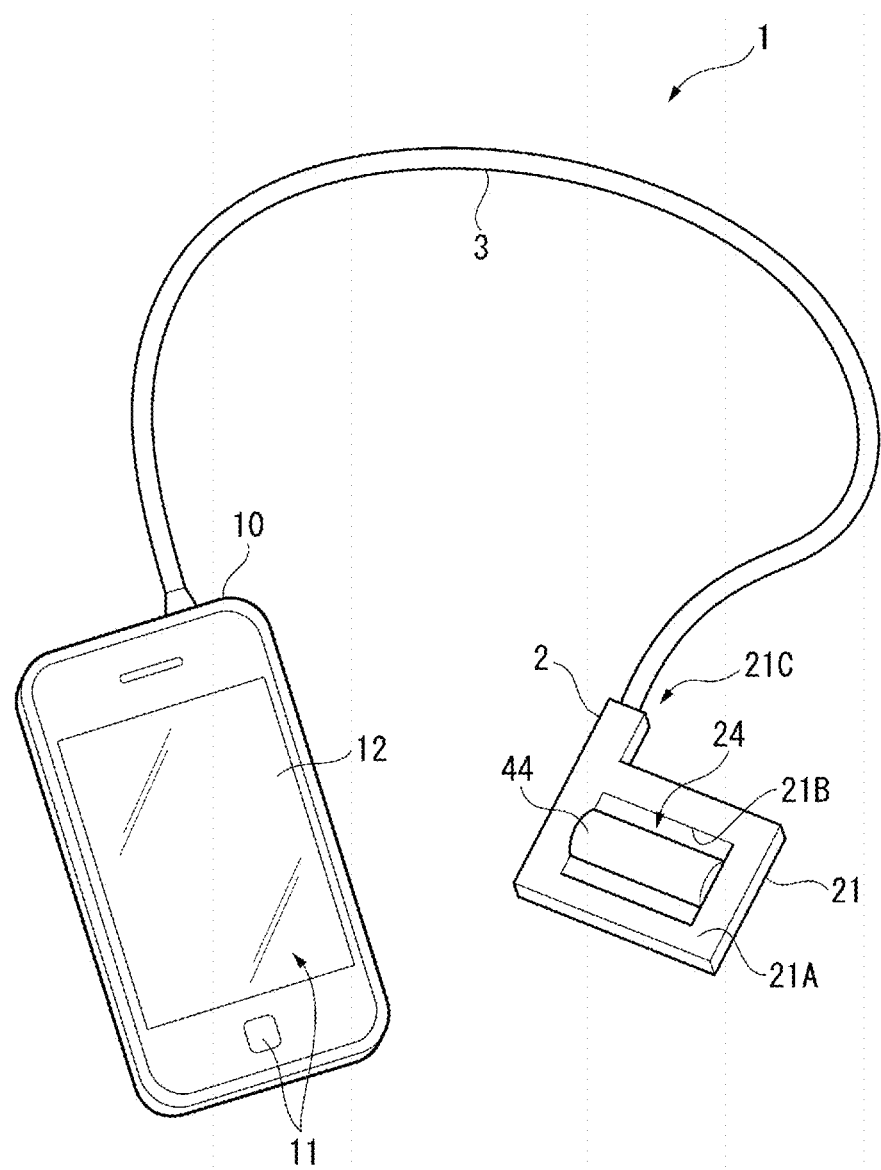
FIG. 1 is a perspective view showing a general configuration of an ultrasonic measurement apparatus according to a first embodiment of the invention.
Figure 2:
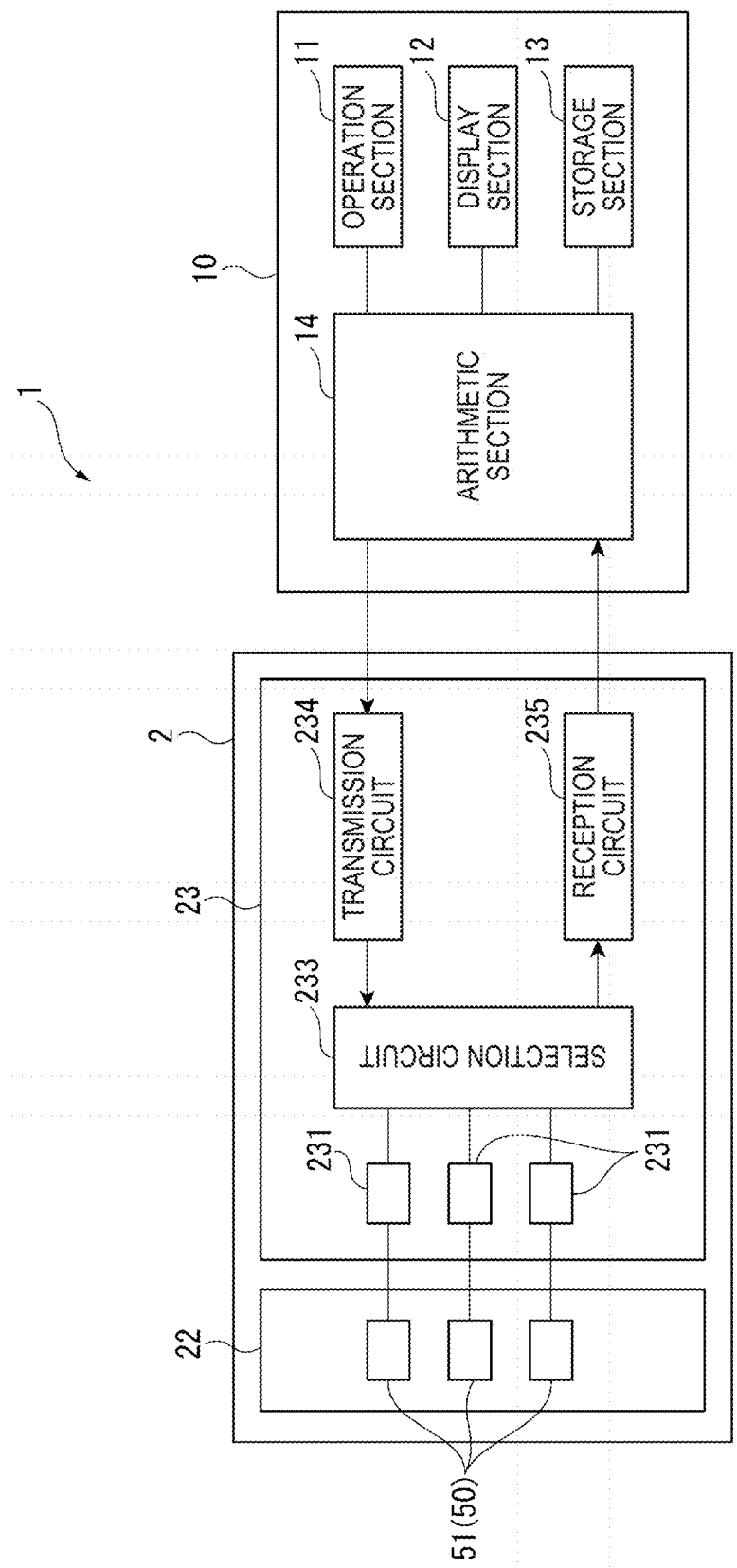
FIG. 2 is a block diagram showing a general configuration of the ultrasonic measurement apparatus according to the first embodiment.

FIG. 1 is a perspective view showing a general configuration of an ultrasonic measurement apparatus 1 according to the present embodiment. FIG. 2 is a block diagram showing a general configuration of the ultrasonic measurement apparatus 1.

As shown in FIG. 1, the ultrasonic measurement apparatus 1 according to the present embodiment is provided with an ultrasonic probe 2, and a control device 10 electrically connected to the ultrasonic probe 2 via a cable 3.

The ultrasonic measurement apparatus 1 transmits an ultrasonic wave from the ultrasonic probe 2 to the inside of a living body (e.g., a human body) with the ultrasonic probe 2 having contact with a surface of the living body. Further, the ultrasonic measurement apparatus 1 receives the ultrasonic wave reflected by apart in the living body using the ultrasonic probe 2, and then, for example, obtains an internal tomographic image in the living body and measures the state (e.g., blood flow) of the part in the living body based on the received signal.

Configuration of Ultrasonic Probe 2

Figure 3:
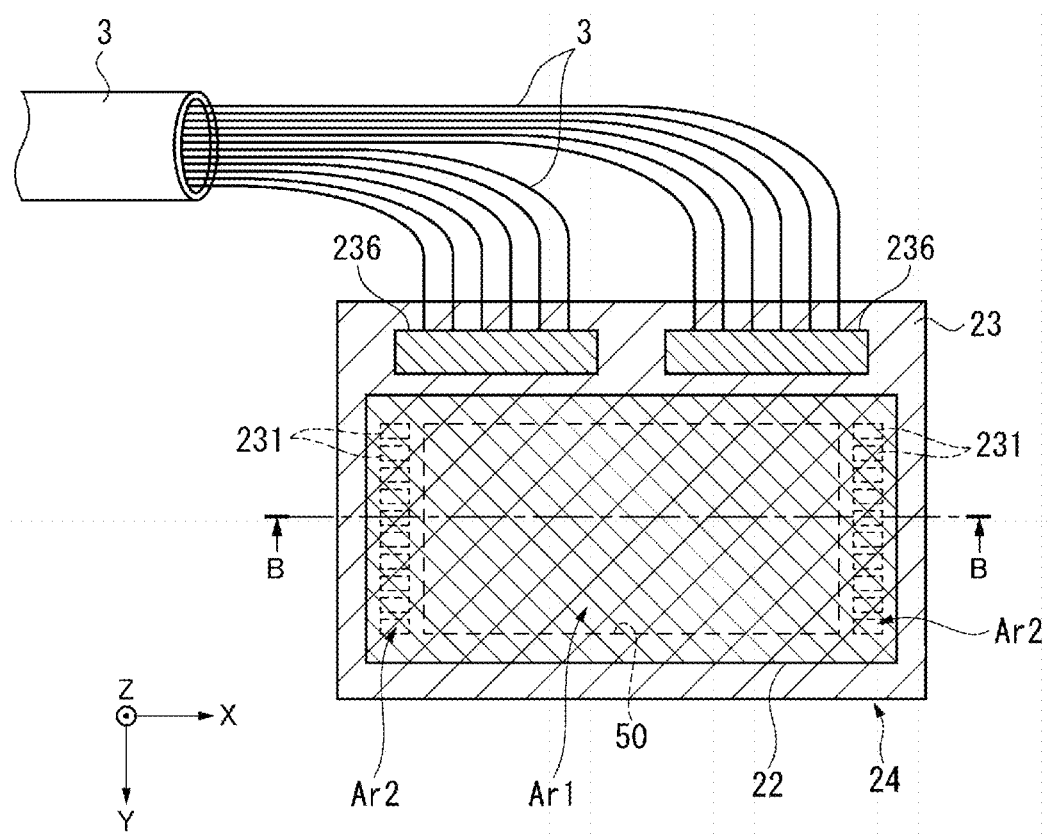
FIG. 3 is a plan view showing a general configuration of an ultrasonic sensor in the ultrasonic probe of the first embodiment.

FIG. 3 is a plan view showing a general configuration of an ultrasonic sensor 24 in the ultrasonic probe 2.

As shown in FIGS. 1 through 3, the ultrasonic probe 2 is provided with a housing 21, an ultrasonic device 22 disposed inside the housing 21, and a wiring board 23 provided with a driver circuit for controlling the ultrasonic device 22 and so on. It should be noted that the ultrasonic sensor 24 is constituted by the ultrasonic device 22 and the wiring board 23, and the ultrasonic sensor 24 constitutes an ultrasonic module according to the invention.

As shown in FIG. 1, the housing 21 is formed to have a box-like shape having a rectangular planar shape, and on one surface (a sensor surface 21A) perpendicular to the thickness direction, there is disposed a sensor window 21B, and a part of the ultrasonic device 22 is exposed therefrom. Further, in a part (a side surface in the example shown in FIG. 1) of the housing 21, there is disposed a through hole 21C for the cable 3, and the cable 3 is connected to the wiring board 23 located inside the housing 21 through the through hole 21C. Further, the gap between the cable 3 and the through hole 21C is filled with, for example, a resin material to thereby ensure the waterproof property.

It should be noted that although in the present embodiment, there is shown a configuration example in which the ultrasonic probe 2 and the control device 10 are connected to each other using the cable, the configuration is not limited to this example, and it is also possible to, for example, connect the ultrasonic probe 2 and the control device 10 to each other with wireless communication, or dispose a variety of constituents of the control device 10 inside the ultrasonic probe 2.

Configuration of Ultrasonic Device 22

Figure 4:
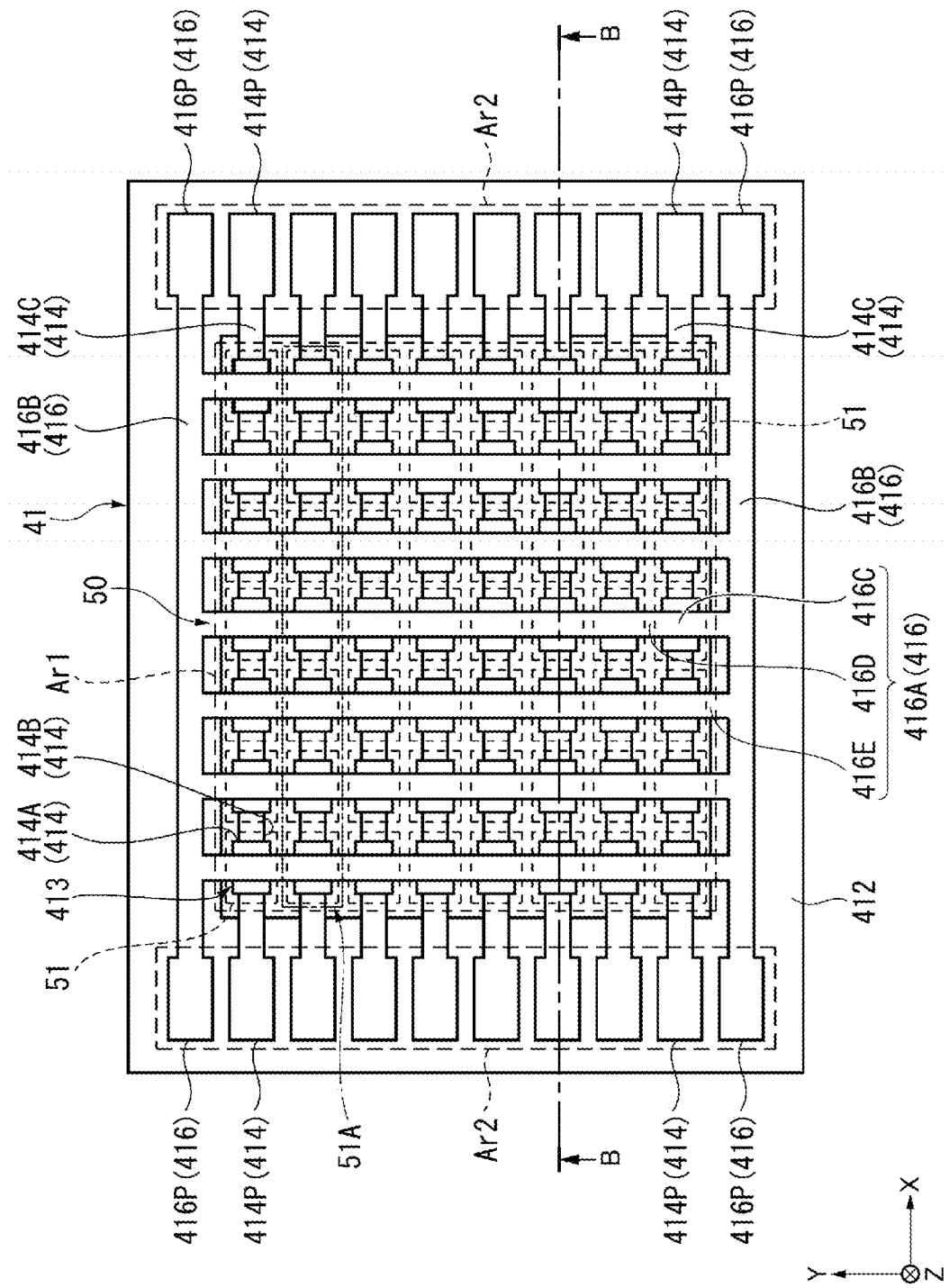
FIG. 4 is a plan view of an element substrate of the ultrasonic sensor according to the first embodiment viewed from a sealing plate side.
Figure 5:
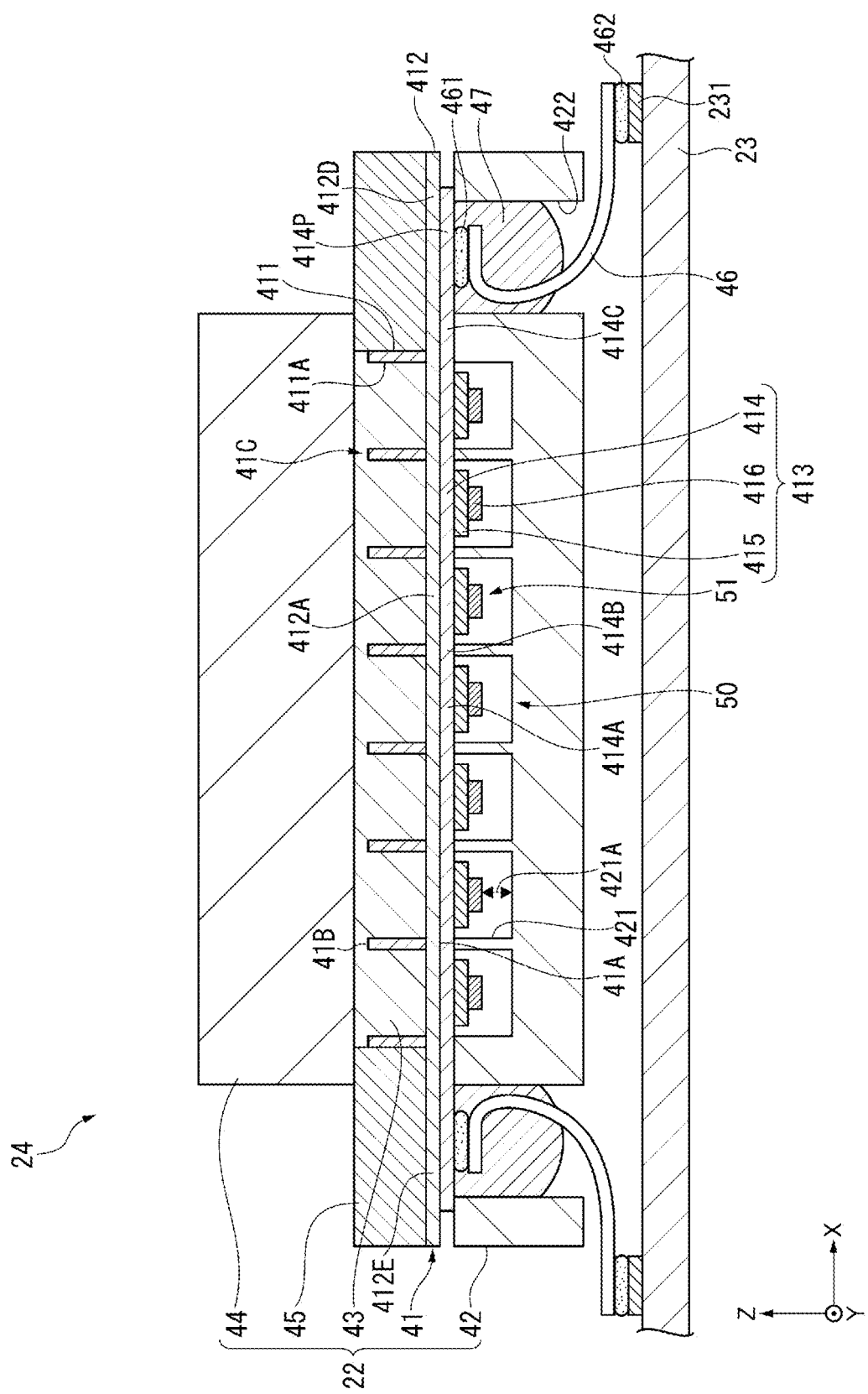
FIG. 5 is a cross-sectional view of the ultrasonic sensor according to the first embodiment.
Figure 6:
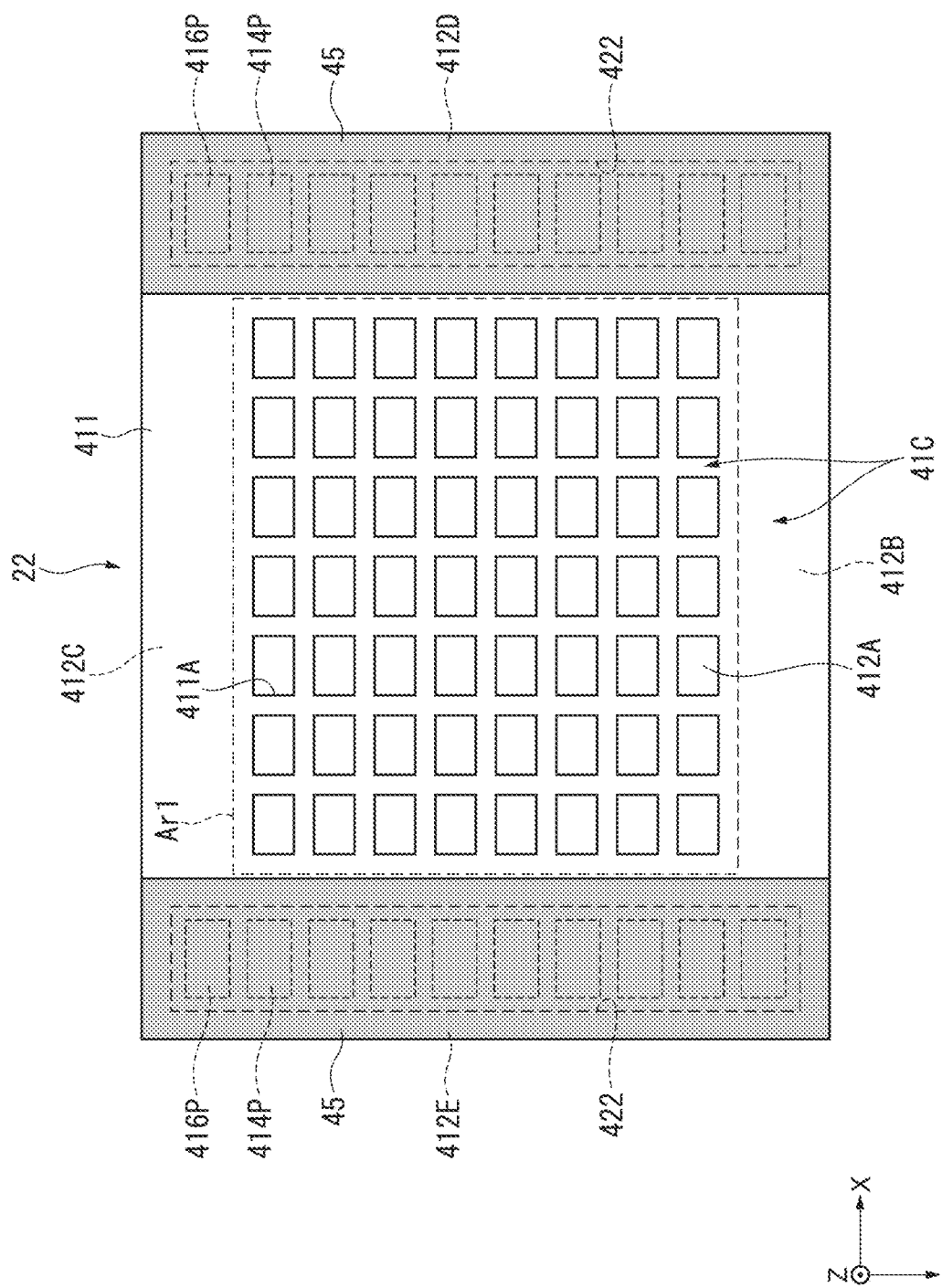
FIG. 6 is a plan view of an ultrasonic device according to the first embodiment viewed from an acoustic lens side.

FIG. 4 is a plan view of an element substrate 41 in the ultrasonic device 22 viewed from a sealing plate 42 side. FIG. 5 is a cross-sectional view of the ultrasonic sensor 24 cut along the line B-B shown in FIG. 4. FIG. 6 is a plan view of the ultrasonic device 22 viewed from an acoustic lens 44 side. It should be noted that in FIG. 6, an acoustic matching layer 43 and the acoustic lens 44 are omitted from the drawing.

As shown in FIG. 5, the ultrasonic device 22 constituting the ultrasonic sensor 24 is constituted by the element substrate 41, the sealing plate 42, the acoustic matching layer 43, the acoustic lens 44, and reinforcing plates 45.

Configuration of Element Substrate 41

As shown in FIGS. 5 and 6, the element plate 41 is formed to have a rectangular shape in a planar view (a planar view viewed from the normal direction) viewed from the thickness direction. The element substrate 41 is provided with a substrate main body part 411, a vibrating film 412 stacked on the substrate main body part 411, and piezoelectric elements 413 stacked on the vibrating film 412.

Further, in the planar view described above, in a central area of the element substrate 41, there is disposed an ultrasonic transducer array 50 (see FIG. 4) having a plurality of ultrasonic transducers 51 described later arranged in an array. The area where the ultrasonic transducer array 50 is disposed is hereinafter referred to as an array region Ar1.

It should be noted that in the following explanation, in the planar view described above, a direction along the longitudinal direction of the element substrate 41 is defined as an X direction, and a direction perpendicular to the X direction is defined as a Y direction. Further, a direction perpendicular to the X direction and the Y direction is defined as a Z direction. It should be noted that one of the directions in the X direction is defined as a +X direction, and an opposite direction to the +X direction is defined as a −X direction. Further, one of the directions in the Y direction is defined as a +Y direction, and an opposite direction to the +Y direction is defined as a −Y direction. Further, a direction from the sealing plate 42 toward the acoustic lens 44 in the Z direction is defined as a +Z direction, and an opposite direction to the +Z direction is defined as a −Z direction.

Here, the X direction corresponds to a first direction according to the invention, and the Y direction corresponds to a second direction according to the invention. Further, a rear surface 41A on the −Z side of the element substrate 41 forms a first surface according to the invention, and an operation surface 41B on the opposite side to the rear surface 41A forms a second surface according to the invention.

The substrate main body part 411 is a semiconductor substrate made of, for example, Si. Inside the array region Ar1 of the substrate main body part 411, there are disposed opening parts 411A corresponding respectively to the ultrasonic transducers 51. Further, the opening parts 411A are closed by the vibrating film 412 disposed on the −Z side of the substrate main body part 411.

The vibrating film 412 is formed of, for example, $SiO_2$ or a laminated body of $SiO_2$ and $ZrO_2$. Further, the vibrating film 412 overlaps the array region Ar1 in the plan view described above, and has vibrating parts 412A for covering the respective opening parts 411A of the substrate main body parts 411. Further, the vibrating film 412 has an extending part 412B (see FIG. 6) extending outward from the edge in the +Y direction of the vibrating parts 412A, and an extending part 412C (see FIG. 6) extending outward from the edge in the −Y direction of the vibrating parts 412A in the planar view described above. Further, the vibrating film 412 has an extending part 412D extending outward from the edge in the +X direction of the vibrating parts 412A and the extending parts 412B, 412C, and an extending part 412E extending outward from the edge in the −X direction of the vibrating parts 412A and the extending parts 412B, 412C in the planar view described above.

Here, the surfaces on the +Z side of the vibrating parts 412A and the extending parts 412B, 412C, 412D, and 412E are located on the same plane. Further, the extending parts 412B, 412C overlap the substrate main body part 411 in the planar view described above, and the extending parts 412D, 412E (are exposed from the substrate main body part 411) do not overlap the substrate main body part 411.

The thickness dimension of the vibrating film 412 becomes sufficiently small one with respect to the substrate main body part 411. In the case of forming the substrate main body part 411 using Si and forming the vibrating film 412 using $SiO_2$, by performing an oxidation treatment on, for example, the surface on the −Z side of the substrate main body part 411, it becomes possible to easily form the vibrating film 412 having a desired thickness dimension. Further, in this case, by performing an etching treatment on the substrate main body part 411 using the vibrating film 412 made of $SiO_2$ as an etching stopper, it becomes possible to easily form the opening parts 411A, and at the same time, expose the extending parts 412D, 412E in the vibrating film 412 from the substrate main body part 411.

Here, in the element substrate 41, a part, in which the vibrating film 412 and the substrate main body part 411 overlap each other in the thickness direction, and the opening parts 411A are not disposed, constitutes a reference thickness part 41C according to the invention having a predetermined reference thickness dimension. Further, the extending parts 412D, 412E exposed from the substrate main body part 411 each constitute a thin part according to the invention having a thickness dimension smaller than that of the reference thickness part 41C. It should be noted that the thickness dimension of the reference thickness part 41C is approximately 80 μm in the present embodiment.

Further, on the vibrating part 412A, there are disposed piezoelectric elements 413 each of which is a laminated body of a lower-part electrode 414, a piezoelectric film 415, and an upper-part electrode 416. Here, the vibrating part 412A and the piezoelectric element 413 constitute an ultrasonic transducer 51 according to the invention.

In such an ultrasonic transducer 51, by applying a rectangular-wave voltage having a predetermined frequency between the lower-part electrode 414 and the upper-part electrode 416, it is possible to vibrate the vibrating part 412A in an opening region of the opening part 411A to transmit the ultrasonic wave. Further, when the vibrating part 412A is vibrated by the ultrasonic wave reflected by an object, a potential difference occurs between an upper part and a lower part of the piezoelectric film 415. Therefore, by detecting the potential difference occurring between the lower-part electrode 414 and the upper-part electrode 416, it becomes possible to detect the ultrasonic wave received.

Further, in the present embodiment, as shown in FIG. 4, a plurality of such ultrasonic transducers 51 as described above is arranged in the array region Ar1 of the element substrate 41 along the X direction and the Y direction.

Here, the lower-part electrode 414 (a signal line according to the invention) is formed to have a straight-line shape along the X direction. Specifically, the lower-part electrode 414 is constituted by lower-part electrode main bodies 414A, each of which is disposed straddling the plurality of ultrasonic transducers 51 arranged along the X direction, and located between the piezoelectric films 415 and the vibrating film 412, lower-part electrode lines 414B each connecting the lower-part electrode main bodies 414A adjacent to each other, and lower-part terminal electrode lines 414C each drawn to one of terminal regions Ar2 located outside the array region Ar1 and in the respective extending parts 412D, 412E. Therefore, in the ultrasonic transducers 51 arranged in the X direction, the lower-part electrodes 414 are in the same potential.

Further, the lower-part terminal electrode lines 414C each extend to the terminal region Ar2 located outside the array region Ar1, and respectively constitute first electrode pads 414P to be connected to electrodes of an FPC 46 described later in the terminal region Ar2.

On the other hand, the upper-part electrode 416 has element electrode parts 416A each disposed straddling the plurality of ultrasonic transducers 51 arranged along the Y direction, and common electrode parts 416B each connecting end parts of the element electrode parts 416A extending in parallel to each other. The element electrode parts 416A each have upper-part electrode main bodies 416C each stacked on the piezoelectric film 415, upper-part electrode lines 416D each connecting the upper-part electrode main bodies 416C adjacent each other, and upper-part terminal electrodes 416E extending outward along the Y direction from the respective ultrasonic transducers 51 disposed on the both end parts in the Y direction.

The common electrode parts 416B are disposed respectively in an end part in the +Y direction and an end part in the −Y direction of the array region Ar1. The common electrode part 416B located on the +Y side connects the upper-part terminal electrodes 416E to each other, which extend in the +Y direction from the ultrasonic transducers 51 disposed in the end part located on the +Y side out of the plurality of ultrasonic transducers 51 disposed along the Y direction. The common electrode part 416B located on the −Y side connects the upper-part terminal electrodes 416E extending on the −Y side to each other. Therefore, in the ultrasonic transducers 51 located inside the array region Ar1, the upper-part electrodes 416 are in the same potential. Further, the pair of common electrode parts 416B described above are disposed along the X direction, and the end parts are each drawn from the array region Ar1 to the terminal region Ar2. Further, the common electrode parts 416B constitute second electrode pads 416P to be connected to the electrodes of the FPC 46 described later in the terminal region Ar2. Here, the second electrode pads 416P and the first electrode pads 414P described above constitute a terminal part according to the invention.

In such an ultrasonic transducer array 50 as described above, there is formed a one-dimensional array structure in which the ultrasonic transducers 51 connected by the lower-part electrode 414 to each other and arranged in the X direction constitute one ultrasonic transducer group 51A functioning as one channel, and the plurality of ultrasonic transducer groups 51A is arranged along the Y direction. Specifically, the X direction corresponds to a slicing direction of the ultrasonic transducer array 50, and the Y direction corresponds to a scanning direction of the ultrasonic transducer array 50.

Configuration of Sealing Plate 42

As shown in FIG. 5, the sealing plate 42 is formed to have the same planar shape when viewed from the thickness direction as that of, for example, the element substrate 41, and is formed of a semiconductor substrate such as a silicon substrate, or an insulator substrate. It should be noted that the material and the thickness of the sealing plate 42 affect the frequency characteristics of the ultrasonic transducer 51, and are therefore preferably set based on the central frequency of the ultrasonic wave transmitted/received by the ultrasonic transducer 51.

Further, the sealing plate 42 is provided with a plurality of concave grooves 421, which correspond respectively to the opening parts 411A of the element substrate 41, formed in an area facing the array region Ar1 of the element substrate 41. Thus, it results that a gap 421A having a predetermined dimension is provided between the element substrate 41 and the area (inside the opening part 411A) vibrated by the ultrasonic transducer 51 in the vibrating part 412A, and the vibration of the vibrating part 412A is prevented from being hindered. Further, it is possible to suppress the problem (cross talk) that the back wave from one ultrasonic transducer 51 enters another ultrasonic transducer 51 adjacent to that ultrasonic transducer 51.

Further, when the vibrating part 412A vibrates, an ultrasonic wave is also emitted toward the sealing plate 42 side as the back wave in addition to the opening part 411A side. The back wave is reflected by the sealing plate 42, and then emitted again toward the vibrating film 412 side via the gap 421A. On this occasion, if the phase of the reflected back wave and the phase of the ultrasonic wave emitted from the vibrating film 412 toward the operation surface 41B side are shifted from each other, the ultrasonic wave is attenuated. Therefore, in the present embodiment, the groove depth of each of the concave grooves 421 is set so that the acoustic distance in the gap 421A becomes an odd multiple of a quarter ($\lambda/4$) of the wavelength $\lambda$ of the ultrasonic wave. In other words, the thickness dimensions of the variety of parts of the element substrate 41 and the sealing plate 42 are set taking the wavelength $\lambda$ of the ultrasonic wave emitted from the ultrasonic transducers 51 into consideration.

Further, the sealing plate 42 is provided with through holes 422, which penetrate the sealing plate 42 in the thickness direction, and expose the respective electrode pads 414P, 416P disposed in the terminal regions Ar2 of the element substrate 41, disposed at positions opposed to the terminal regions Ar2 of the element substrate 41. Further, the electrode pads 414P, 416P are respectively connected to the electrodes of the FPC 46 described later and inserted in the through holes 422.

Configuration of FPC 46

The FPC 46 are each configured by disposing a wiring pattern on a film having flexibility. The FPC 46 each have one end part inserted in the through hole 422 of the sealing plate 42, and the electrodes disposed on the one end part are bonded to the respective electrode pads 414P, 416P of the element substrate 41 with an electrically-conductive bonding material 461 such as solder.

Further, the FPC 46 each have the other end part located outside the through hole 422, and the electrodes disposed on the other end part are bonded to respective wiring terminal parts 231 of the wiring board 23 described later with an electrically-conductive bonding material 462 such as solder. Thus, the electrode pads 414P, 416P and the wiring terminal parts 231 are electrically connected to each other, respectively. Here, the FPC 46 each constitute a connection member according to the invention.

Further, connection part between the electrode pads 414P, 416P and each of the FPC 46 is covered with a protective member 47 made of, for example, resin filling the through hole 422 of the sealing plate 42, and protecting the connection part. Thus, the exfoliation and electrolytic corrosion of the connection parts can be prevented.

Configuration of Reinforcing Plates 45

As shown in FIGS. 5 and 6, the reinforcing plates 45 are disposed covering the surfaces on the +Z side of the extending parts 412D, 412E of the element substrate 41, respectively. In other words, the reinforcing plates 45 are respectively disposed along the Y direction on the both ends in the X direction of the array region Ar1 in the planar view described above. Thus, the reinforcing plates 45 overlap the electrode pads 414P, 416P of the element substrate 41 and the respective through holes 422 provided to the sealing plate 42 in the planar view described above.

Further, the reinforcing plates 45 are higher in bending rigidity (harder) than the element substrate 41 (the substrate main body part 411 and the vibrating film 412). In the present embodiment, the reinforcing plates 45 are each formed of a metal plate made of, for example, 42-alloy. It should be noted that as the reinforcing plates 45, it is also possible to use a plate other than the metal plate, such as a ceramic plate providing the plate is higher in bending rigidity than the element substrate 41.

Further, the thickness dimension of the reinforcing plates 45 is larger than the thickness dimension of the reference thickness part 41C of the element substrate 41. Therefore, the surfaces (reinforcing plate surfaces) on the +Z side of the reinforcing plates 45 are located on the +Z side with respect to the surface (the same surface as the opening surface of the opening parts 411A) on the +Z side of the substrate main body part 411.

It should be noted that the reinforcing plates 45 are attached to the element substrate 41 provided with the sealing plate 42 after the sealing plate 42 is disposed on the element substrate 41.

Configuration of Acoustic Matching Layer 43 and Acoustic Lens 44

The acoustic matching layer 43 is formed so as to fill the opening parts 411A of the element substrate 41, and to have a predetermined thickness dimension from the surface on the +Z side of the substrate main body part 411. Here, the surface on the +Z side of the acoustic matching layer 43 is located on the same plane as the surface (the reinforcing plate surface) on the +Z side of the reinforcing plate 45.

The acoustic lens 44 is disposed on the surface on the +Z side of the acoustic matching layer 43, and as shown in FIG. 1, exposed to the outside from the sensor window 21B of the housing 21.

The acoustic matching layer 43 and the acoustic lens 44 efficiently propagate the ultrasonic wave emitted from the ultrasonic transducers 51 to the living body as the measurement object, and further propagate the ultrasonic wave, which has been reflected in the living body, to the ultrasonic transducers 51 with efficiency. Therefore, the acoustic matching layer 43 and the acoustic lens 44 are set to have an acoustic impedance intermediate between the acoustic impedance of the ultrasonic transducers 51 of the element substrate 41 and the acoustic impedance of the living body.

Configuration of Wiring Board 23

As shown in FIG. 5, the wiring board 23 has the wiring terminal parts 231 corresponding respectively to the electrodes of the FPC 46, and the electrodes of the FPC 46 are bonded to the wiring terminal parts 231 with the electrically-conductive bonding member 462 such as solder.

Further, the wiring board 23 is provided with a driver circuit for driving the ultrasonic device 22, and so on. Specifically, as shown in FIGS. 2 and 3, the wiring board 23 is provided with a selection circuit 233, a transmission circuit 234, a reception circuit 235, a connector part 236, and so on.

The selection circuit 233 switches between transmission connection of connecting the ultrasonic device 22 and the transmission circuit 234 to each other, and reception connection of connecting the ultrasonic device 22 and the reception circuit 235 to each other based on the control of the control device 10.

The transmission circuit 234 outputs a transmission signal, which represents the fact that the ultrasonic device 22 is made to transmit the ultrasonic wave via the selection circuit 233 when switching to the transmission connection is made due to the control of the control device 10.

The reception circuit 235 outputs a reception signal, which is input from the ultrasonic device 22, to the control device 10 via the selection circuit 233 when switching to the reception connection is made due to the control of the control device 10. The reception circuit 235 is configured including, for example, a low-noise amplifier circuit, a voltage-controlled attenuator, a programmable-gain amplifier, a low-pass filter, and an A/D converter, and performs a variety of signal processing such as conversion of the reception signal to a digital signal, elimination of a noise component, and amplification to a desired signal level, and then outputs the reception signal thus processed to the control device 10.

The connector part 236 is connected to the transmission circuit 234 and the reception circuit 235. Further, the cable 3 is connected to the connector part 236, and as described above, the cable 3 is drawn through the through hole 21C of the housing 21 and is then connected to the control device 10.

Method of Mounting Ultrasonic Device 22 on Wiring Board 23

FIGS. 7A through 7D are diagrams showing a method of mounting the ultrasonic device 22 according to the present embodiment on the wiring board 23.

Figure 7A:
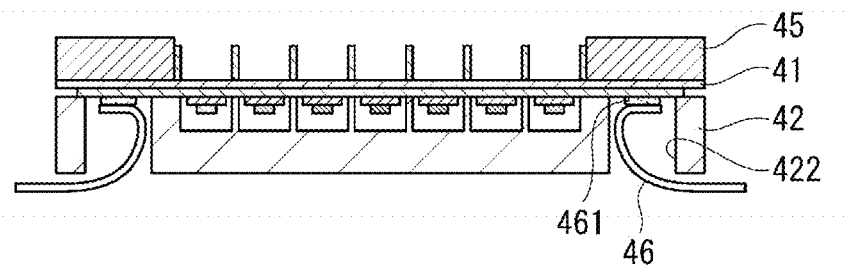
FIGS. 7A through 7D are diagrams showing a method of mounting the ultrasonic device according to the first embodiment on the wiring board.

Firstly, as shown in FIG. 7A, one end parts of the FPC 46 are inserted in the respective through holes 422 of the sealing plate 42, and then the electrodes in the one end part are respectively bonded to the electrode pads 414P, 416P of the element substrate 41 with the bonding member 461 with respect to the ultrasonic device 22, which has not been provided with the acoustic matching layer 43 and the acoustic lens 44. On this occasion, the bonding member 461 contracts due to the heat, and a stress is applied to the element substrate 41 in some cases. Alternatively, there is also a possibility that the element substrate 41 itself is contracted by the heat generated when making the bonding member 461 in the melted state have contact with each of the electrode pads 414P, 416P. Even in such a case, the warp of the element substrate 41 is suppressed due to the reinforcing plates 45 provided to the element substrate 41.

Figure 7B:
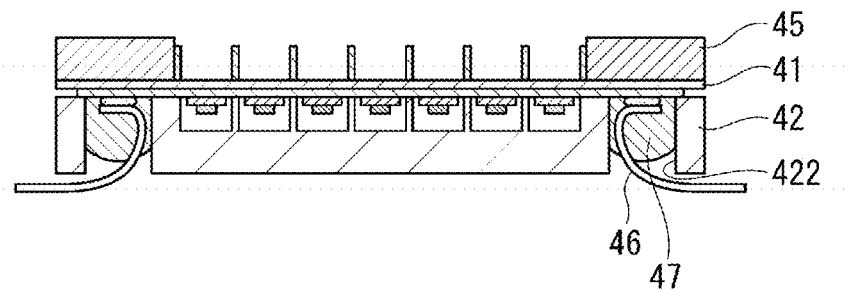

Then, as shown in FIG. 7B, the through holes 422 of the sealing plate 42 are filled with the protective member 47 in the state of being softened by the heat. Subsequently, the protective member 47 is hardened and is contracted as the temperature drops. On this occasion, the stress is applied to the element substrate 41 due to the contraction of the protective member 47. Even in this case, the warp of the element substrate 41 is suppressed due to the reinforcing plates 45.

Figure 7C:
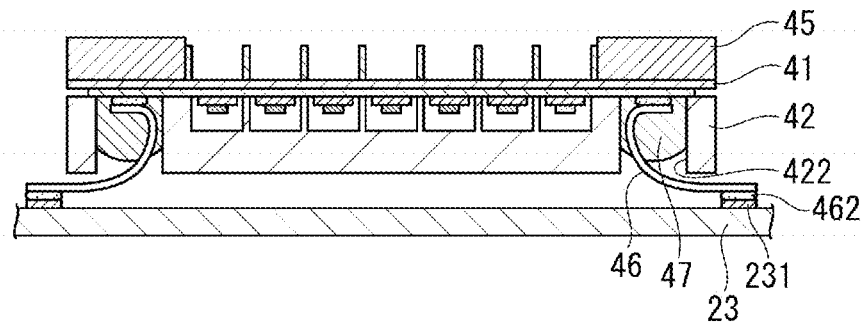

Then, as shown in FIG. 7C, the electrodes in the other side of the FPC are bonded to the wiring terminal parts 231 of the wiring board 23 with the bonding member 462. On this occasion, there is a possibility that the heat applied is conducted to the FPC 46 to contract the bonding member 461, the protective member 47, and the element substrate 41 itself. Even in such a case, the warp of the element substrate 41 is suppressed due to the reinforcing plates 45 provided to the element substrate 41.

Figure 7D:
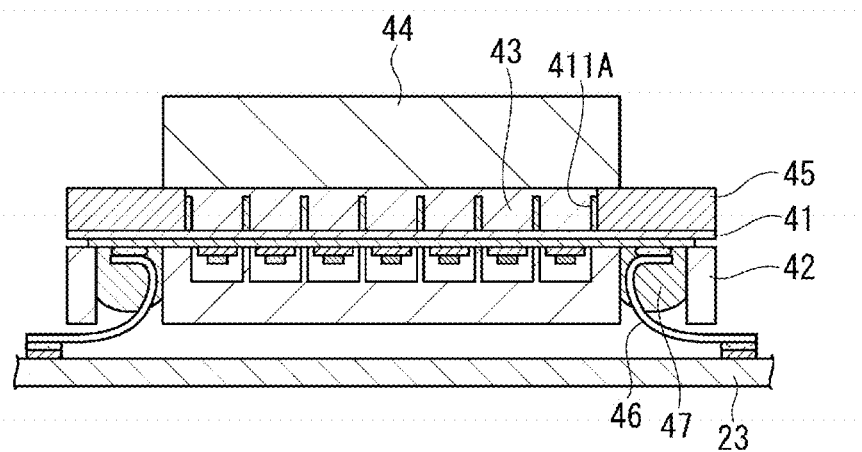

Subsequently, as shown in FIG. 7D, the opening parts 411A of the element substrate 41 are filled with a material (e.g., silicone) for forming the acoustic matching layer 43. Then, by removing a surplus part of the filled material along the surface (the reinforcing plate surface) on the +Z side of the reinforcing plate 45, the acoustic matching layer 43 having a uniform thickness dimension with reference to the reinforcing plate surface is formed. Then, the acoustic lens 44 is made to adhere to the surface on the +Z side of the acoustic matching layer 43.

Configuration of Control Device 10

As shown in FIGS. 1 and 2, the control device 10 is configured including, for example, an operation section 11, a display section 12, a storage section 13, and an arithmetic section 14. As the control device 10, there can be used a terminal device such as a tablet terminal, a smartphone, or a personal computer, and the control device 10 can also be a dedicated terminal device for operating the ultrasonic probe 2.

The operation section 11 is a user interface (UI) for the user to operate the ultrasonic measurement apparatus 1, and can be formed of, for example, a touch panel or operation buttons disposed on the display section 12, a keyboard, or a mouse.

The display section 12 is formed of, for example, a liquid crystal display, and displays an image.

The storage section 13 stores a variety of programs and a variety of data for controlling the ultrasonic measurement apparatus 1.

The arithmetic section 14 is formed of an arithmetic circuit such as a central processing unit (CPU), and a storage circuit such as a memory. Further, the arithmetic section 14 retrieves and then performs the variety of programs stored in the storage section 13 to perform control of a process of generating and outputting the transmission signal on the transmission circuit 234, and to perform control of frequency setting and gain setting of the reception signal on the reception circuit 235.

Functions and Advantages of First Embodiment

In the present embodiment, the reinforcing plates 45 higher in bending rigidity than the element substrate 41 are respectively disposed on the surfaces on the +Z side of the extending parts 412D, 412E of the element substrate 41 and in the regions overlapping the electrode pads 414P, 416P in the planar view described above. According to this configuration, since the regions corresponding to the electrode pads 414P, 416P of the element substrate 41 are reinforced by the reinforcing plates 45, even if the stress is applied to the element substrate 41 in the mounting process as described above, the warp of the element substrate 41 can be suppressed. Thus, the possibility that a crack or the like occurs in the element substrate 41 can be reduced.

In the present embodiment, since the reinforcing plates 45 are disposed in the regions respectively overlapping the through holes 422 in the planar view described above, the stress due to the contraction of the protective member 47 with which the through holes 422 are filled can be relaxed, and thus the warp of the element substrate 41 can be suppressed. Further, by filling the through holes 422 with the protective member 47, the protective member 47 is prevented from spreading to regions where the reinforcing plates 45 are not disposed. In other words, it becomes possible to dispose the protective member 47 in the parts which are increased in the bending rigidity to the stress by the reinforcing plates 45, and the warp of the element substrate 41 can also be suppressed in this regard.

In the present embodiment, the reinforcing plates 45 are disposed in the extending parts 412D, 412E small in the thickness dimension of the element substrate 41, and the surfaces on the +Z side of the extending parts 412D, 412E where the reinforcing plates 45 are disposed are located on the −Z side of the surface on the +Z side in the reference thickness part 41C. In other words, the regions where the reinforcing plates 45 are disposed of the element substrate 41 each have a step-like shape toward the −Z side. Therefore, by disposing the reinforcing plates 45 in the parts having the step-like shape described above, the total thickness dimension of the element substrate 41 and the reinforcing plate 45 can be decreased compared to the case of, for example, disposing the reinforcing plates 45 in the regions having the same thickness as the reference thickness part 41C, and thus height reduction of the ultrasonic device 22 can be facilitated.

In the present embodiment, the surfaces on the +Z side of the thin parts (the extending parts 412D, 412E) where the reinforcing plates 45 are disposed are coplanar with the surface facing the opening of the vibrating parts 412A. According to this configuration, in the case of forming the opening parts 411A and the thin parts to the flat substrate for forming the element substrate 41 by performing etching, it is sufficient to perform etching the same in depth to the opening parts 411A and the thin parts. According to this configuration, the opening parts 411A and the thin parts can easily be formed compared to the case of performing etching different in depth between the opening parts 411A and the thin parts.

In the present embodiment, since the reinforcing plates 45 longitudinal along the Y direction are disposed on the both ends in the X direction of the array region Ar1, the regions corresponding to the electrode pads 414P, 416P of the element substrate 41 can easily be covered with the reinforcing plates. In other words, there is no need to dispose the reinforcing plates 45 corresponding respectively to the electrode pads 414P, 416P, and the reinforcing plates 45 can be disposed throughout the plurality of terminal parts arranged in the Y direction, and thus simplification of the configuration can be achieved.

In the present embodiment, the surface (the reinforcing plate surface) on the +Z side of each of the reinforcing plates 45 is located on the +Z side with respect to the opening surfaces in the opening parts 411A. Therefore, when forming the acoustic matching layer 43, it becomes possible to form the acoustic matching layer 43 having the uniform thickness dimension with reference to the reinforcing plate surfaces by filling the opening parts 411A with the material for forming the acoustic matching layer 43, and then removing the surplus part of the material along the reinforcing plate surfaces.

Second Embodiment

Then a second embodiment according to the invention will be described.

In the ultrasonic device 22 according to the first embodiment, the thin parts of the element substrate 41 are disposed on the both ends in the X direction, and the reinforcing plates 45 are respectively disposed in the thin parts. In contrast, an ultrasonic device 22H according to the second embodiment is different in the point that the thin parts are also disposed on both ends in the Y direction of the element substrate, and the reinforcing plate 45 shaped like a frame is disposed so as to cover the whole of the thin parts.

It should be noted that in the following explanation, constituents substantially the same as those of the first embodiment will be denoted by the same reference symbols, and the explanation thereof will be omitted or simplified.

Figure 8:
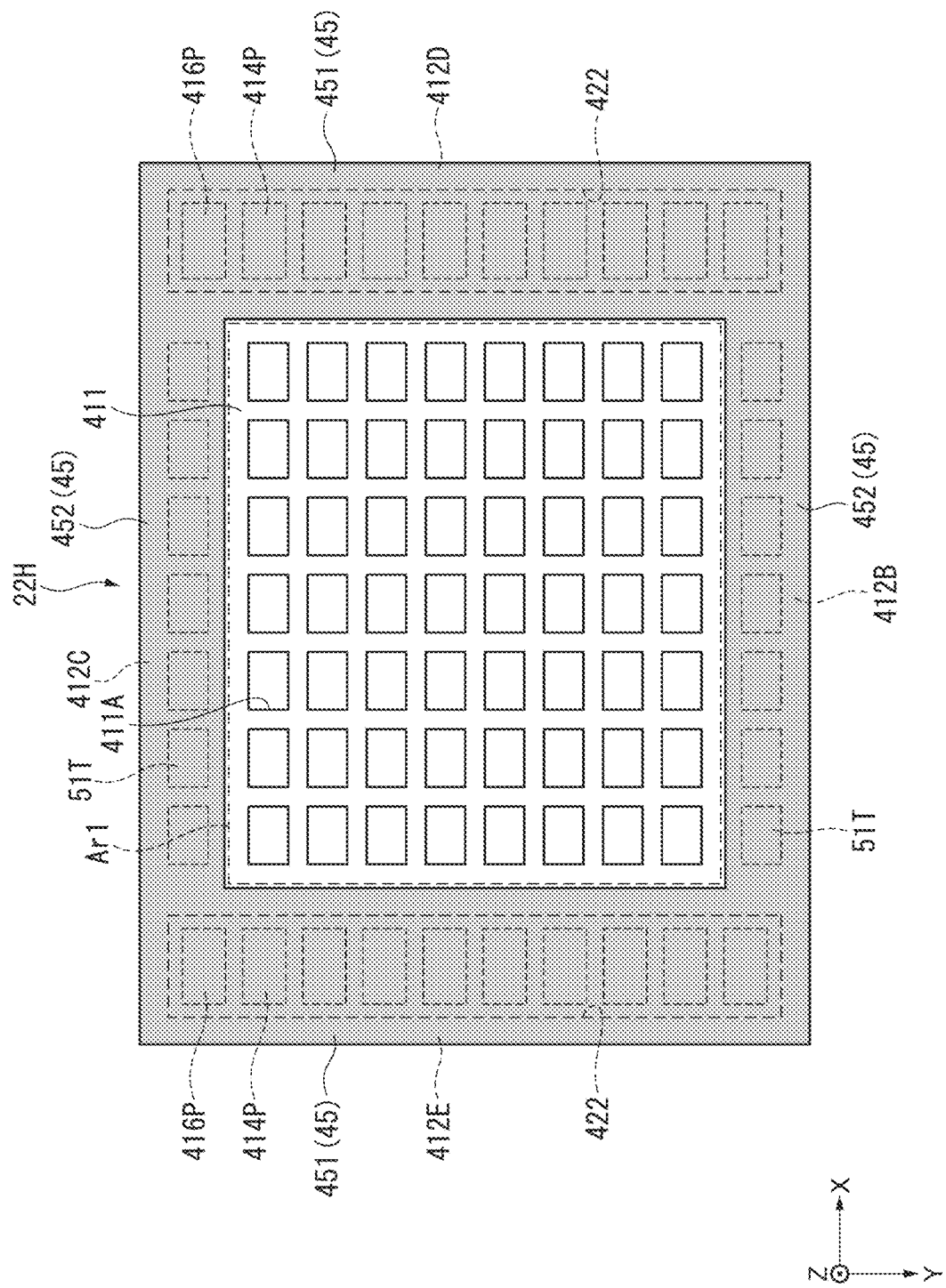
FIG. 8 is a plan view of an ultrasonic device according to a second embodiment of the invention viewed from an acoustic lens side.

FIG. 8 is a plan view of the ultrasonic device 22H according to the second embodiment viewed from the acoustic lens 44 side.

As shown in FIG. 8, in the ultrasonic device 22H, a plurality of evaluating ultrasonic transducers 51T (TEG: Test Element Group) as elements used for product inspection is disposed so as to be arranged along the X direction in the outside in the +Y direction and the outside in the −Y direction of the array region Ar1 of the element substrate in the planar view described above. The evaluating ultrasonic transducers 51T are each configured including, for example, a vibrating part, a piezoelectric element, and an electrode, and are used for a driving evaluation, a burn-in evaluation, and so on of the piezoelectric element.

Further, the substrate main body part 411 is formed so as to overlap only the array region Ar1 in the planar view described above. In other words, not only the extending parts 412D, 412E of the vibrating film 412 but also the extending parts 412B, 412C (are exposed from the substrate main body part 411) do not overlap the substrate main body part 411 in the planar view described above.

Further, the reinforcing plate 45 is formed to have a frame-like shape so as to surround the array region Ar1 of the element substrate in the planar view described above.

Specifically, the reinforcing plate 45 has terminal region reinforcing parts 451 and evaluation element region reinforcing parts 452.

The terminal region reinforcing parts 451 are disposed along the Y direction on the both ends in the X direction of the array region Ar1, and overlap the extending parts 412D, 412E of the vibrating film 412, respectively, in the planar view described above. Thus, the terminal region reinforcing parts 451 overlap the electrode pads 414P, 416P of the element substrate and the respective through holes 422 provided to the sealing plate 42 in the planar view described above.

The evaluation element region reinforcing parts 452 are disposed along the X direction on the both ends in the Y direction of the array region Ar1, and overlap the extending parts 412B, 412C, respectively, in the planar view described above. Thus, the evaluation element region reinforcing parts 452 overlap the evaluating ultrasonic transducers 51T of the element substrate in the planar view described above.

Functions and Advantages of Second Embodiment

According to the present embodiment, substantially the same functions and advantages can be obtained with substantially the same configuration as that of the first embodiment.

Further, in the present embodiment, the reinforcing plate 45 is formed to have a frame-like shape and surrounds the array region Ar1 in the planar view described above. According to this configuration, since the element substrate can more firmly be reinforced compared to the case in which, for example, the reinforcing plates 45 are disposed only on the both ends in the X direction of the array region Ar1, the warp of the element substrate can further be suppressed. For example, the element substrate can further be inhibited from bending along the X direction as the slicing direction.

In the present embodiment, by disposing the evaluation element region reinforcing parts 452 longitudinal along the X direction on the both ends in the Y direction of the array region Ar1, the regions of the element substrate corresponding to the evaluating ultrasonic transducers 51T can easily be covered with the reinforcing plate 45. Further, by covering the regions with the reinforcing plate 45, it is possible to inhibit a crack or the like from occurring in the element substrate in the regions in the case in which, for example, an impact is applied to the ultrasonic device 22H, and thus, breakage of the evaluating ultrasonic transducers 51T can be inhibited.

In the present embodiment, since the reinforcing plate 45 is formed to have the frame-like shape, when filling the opening parts 411A with the material for forming the acoustic matching layer 43, it is possible to stem the material with the reinforcing plate 45. Thus, the acoustic matching layer 43 can easily be formed.

Third Embodiment

Then a third embodiment according to the invention will be described.

In the ultrasonic device 22H according to the second embodiment, the thin parts are also disposed on the both ends in the Y direction of the element substrate in addition to the both ends in the X direction, and the reinforcing plate 45 shaped like a frame is disposed so as to cover the whole of the thin parts. In contrast, an ultrasonic device 22I according to the third embodiment is different mainly in the point that the reinforcing plate 45 is disposed so as to also cover the reference thickness part 41C in addition to the whole of the thin parts.

It should be noted that in the following explanation, constituents substantially the same as those of the first embodiment will be denoted by the same reference symbols, and the explanation thereof will be omitted or simplified.

Figure 9:
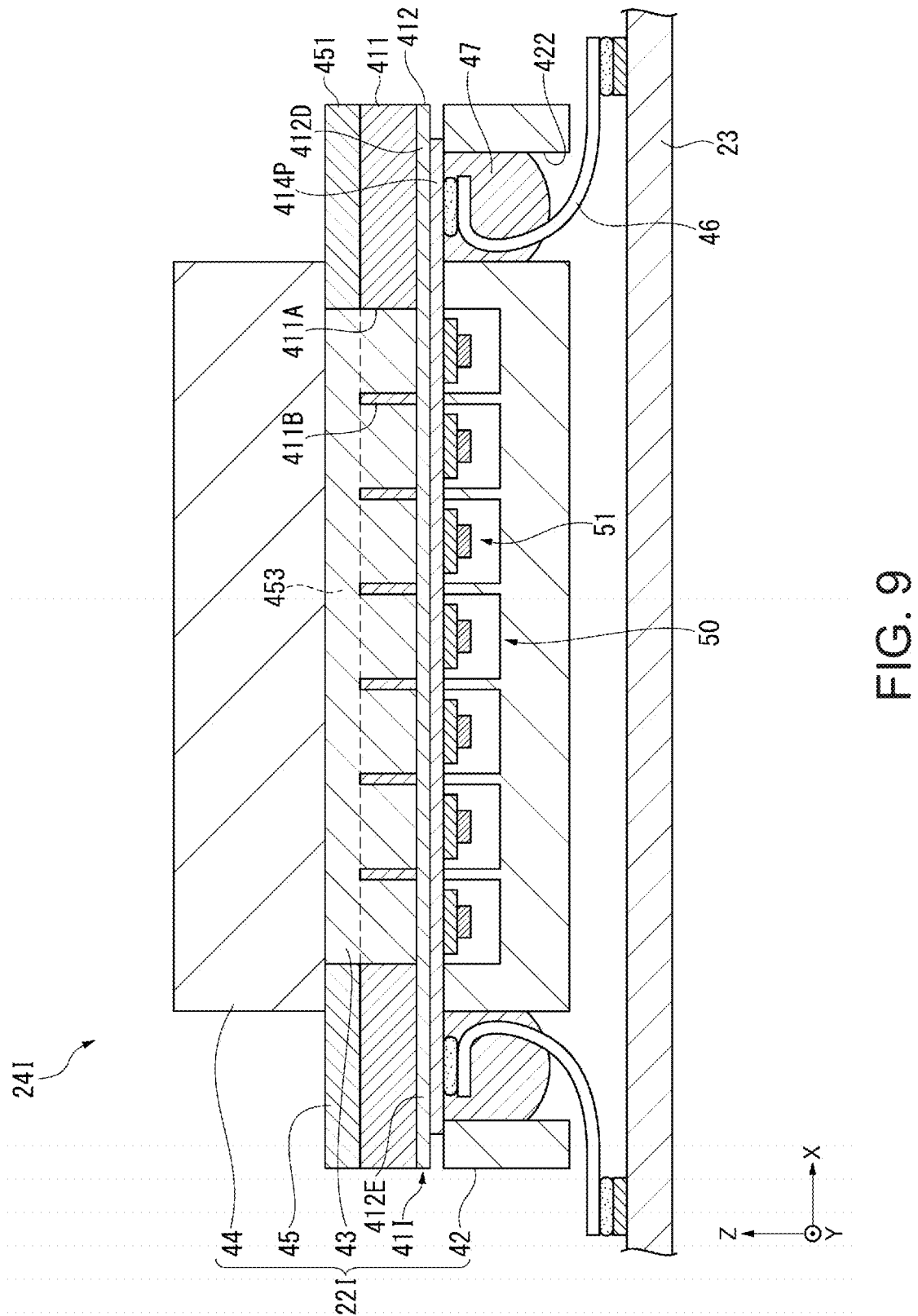
FIG. 9 is a cross-sectional view of an ultrasonic sensor according to a third embodiment of the invention.
Figure 10:
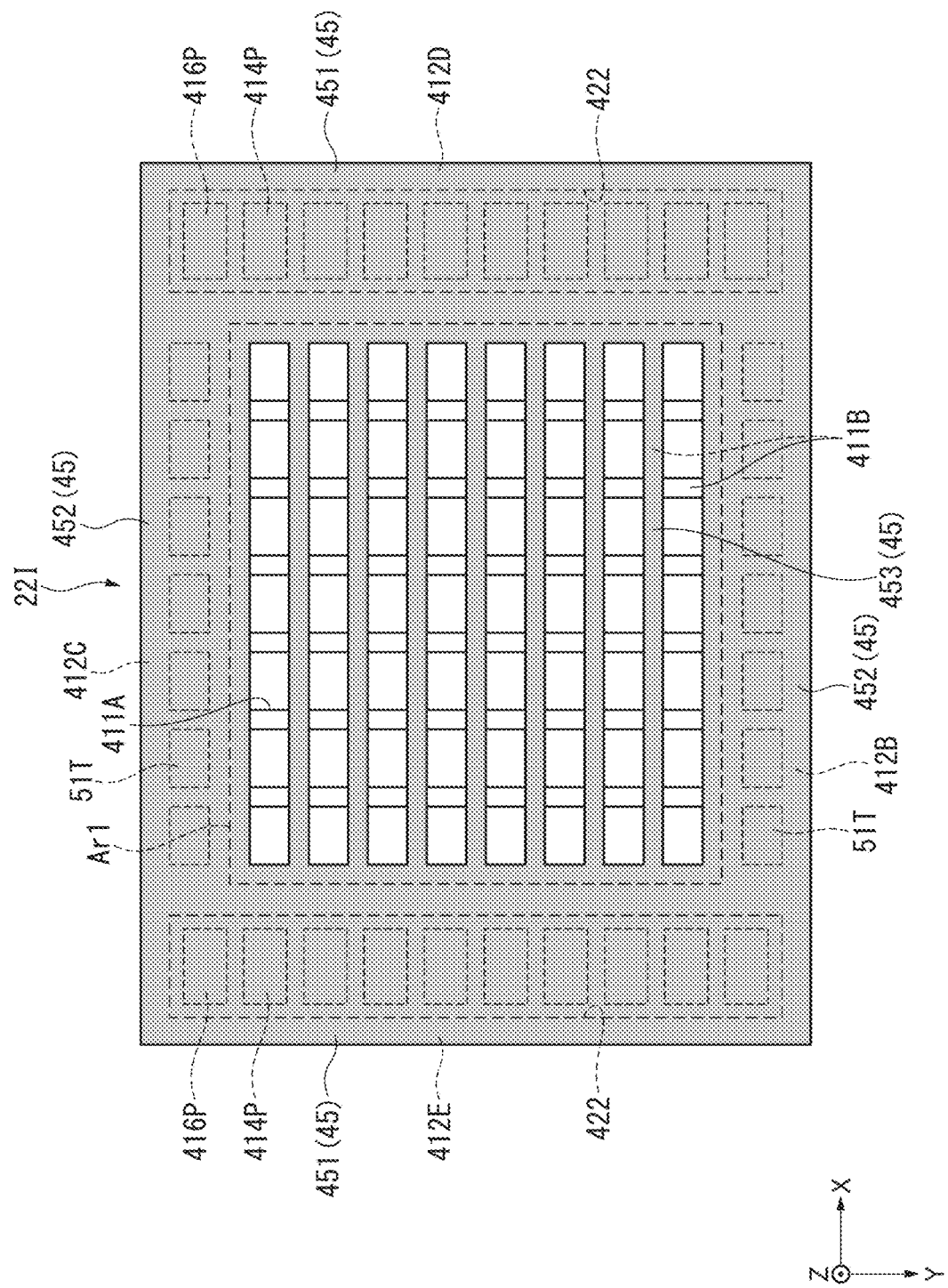
FIG. 10 is a plan view of an ultrasonic device according to the third embodiment viewed from an acoustic lens side.

FIG. 9 is a cross-sectional view of an ultrasonic sensor 24I according to the third embodiment. FIG. 10 is a plan view of the ultrasonic device 22I according to the third embodiment viewed from the acoustic lens 44 side.

As shown in FIG. 10, in the ultrasonic device 22I, similarly to the ultrasonic device 22H according to the second embodiment, a plurality of evaluating ultrasonic transducers 51T is disposed so as to be arranged along the X direction in the outside in the +Y direction and the outside in the −Y direction of the array region Ar1 of an element substrate 411 in the planar view described above.

Further, as shown in FIGS. 9 and 10, in the ultrasonic device 22I, the substrate main body part 411 is formed to have the same shape and the same size as the vibrating film 412 in the planar view described above. In other words, the substrate main body part 411 overlaps not only the extending parts 412B, 412C of the vibrating film 412 but also the extending parts 412D, 412E in the planar view described above.

Further, the reinforcing plate 45 is disposed on the surface on the +Z side of the substrate main body part 411. Specifically, the reinforcing plate 45 has the terminal region reinforcing parts 451 overlapping the extending parts 412D, 412E of the vibrating film 412, and the evaluation element region reinforcing parts 452 overlapping the extending parts 412B, 412C in the planar view described above similarly to the ultrasonic device 22H according to the second embodiment.

Further, the reinforcing plate 45 has inter-element region reinforcing parts 453 for covering partition wall parts 411B in a direction along the X direction out of the partition wall parts 411B corresponding to parts between the opening parts 411A in the substrate main body part 411. In other words, the inter-element region reinforcing parts 453 are each disposed between the ultrasonic transducers 51 arranged in the Y direction in the planar view described above.

Functions and Advantages of Third Embodiment

According to the present embodiment, substantially the same functions and advantages can be obtained with substantially the same configuration as those of the first and second embodiments.

Further, in the present embodiment, the reinforcing plate 45 has the inter-element region reinforcing parts 453, and the inter-element region reinforcing parts 453 are each disposed between the ultrasonic transducers 51 arranged in the Y direction in the planar view described above. According to this configuration, since the element substrate 411 can more firmly be reinforced compared to the case in which the reinforcing plate 45 is not disposed in a part overlapping the array region Ar1, the warp of the element substrate 411 can further be suppressed. In particular, since it is possible to inhibit the ultrasonic transducer array 50 from bending along the X direction as the slicing direction, it is possible to uniform the directions of the ultrasonic waves to be emitted to a predetermined direction between the ultrasonic transducers 51 constituting the ultrasonic transducer group 51A. Further, the cross talk between the ultrasonic transducers 51 arranged in the Y direction, namely between the ultrasonic transducer groups 51A, can also be reduced.

MODIFIED EXAMPLES

It should be noted that the invention is not limited to each of the embodiments described above, but includes modifications and improvements within a range where the advantages of the invention can be achieved, and configurations, which can be obtained by, for example, arbitrarily combining the embodiments.

Although in each of the embodiments described above, there is illustrated the fact that the element substrate warps due to the stress applied to the element substrate due to the contraction of the protective member 47, even in the configuration without, for example, the protective member 47, the warp of the element substrate can be suppressed by applying the invention providing stress is applied to the vicinity of the electrode pads 414P, 416P of the element substrate in the configuration. In the case of, for example, connecting the electrode pads 414P, 416P directly to the wiring board 23 using solder or the like, there is also a possibility that the stress due to the contraction of the solder is applied to the element substrate, or the element substrate itself contracts due to the heat applied when the solder in the melted state has contact with the electrode pads 414P, 416P. Also in this case, by applying the invention, the warp of the element substrate can be suppressed.

Although in each of the embodiments described above, the reinforcing plate 45 overlaps the through holes 422 of the sealing plate 42 in the planar view described above, the invention is not limited to this configuration. Specifically, it is sufficient for the reinforcing plate 45 to overlap at least the electrode pads 414P, 416P in the planar view described above.

Although in each of the embodiments described above, the surface on the +Z side of the region (the reinforced region) of the element substrate where the reinforcing plate 45 is disposed is coplanar with the surface facing the opening parts 411A of the vibrating parts 412A, or the opening surface of the opening parts 411A, the invention is not limited to this configuration. For example, the surface on the +Z side of the reinforced region can also be located between the surface facing the opening parts 411A of the vibrating parts 412A and the opening surface of the opening parts 411A, or can also be located on the +Z side with respect to the opening surface.

Although in each of the embodiments described above, the electrode pads 414P, 416P are disposed on the both ends in the X direction of the array region Ar1, the invention is not limited to this configuration. For example, the electrode pads 414P, 416P can also be disposed only on either one of the +X side and the −X side of the array region Ar1.

Although in the second and the third embodiments described above, the evaluating ultrasonic transducers 51T are disposed on the both ends in the Y direction of the array region Ar1, the invention is not limited to this configuration. Specifically, the evaluating ultrasonic transducers 51T are not required to be disposed.

Further, in the second embodiment, it is also possible to form the substrate main body part 411 so as to overlap the extending parts 412B, 412C of the vibrating film 412 in the planar view described above, to dispose the opening parts in the areas overlapping the extending parts 412B, 412C, and to configure the evaluating ultrasonic transducers 51T each including the vibrating part, the piezoelectric element, the electrode, and the opening part. In this case, it is also possible to evaluate whether the ultrasonic wave is emitted from the ultrasonic transducers, or whether or not the ultrasonic wave can be received in addition to the burn-in evaluation of the piezoelectric elements.

In this case, there is adopted a configuration in which the evaluation element region reinforcing parts 452 are each formed of a separated member from the terminal region reinforcing parts 451, and are disposed on the substrate main body part 411. Alternatively, it is also possible to adopt a configuration in which the evaluation element region reinforcing parts 452 run on the substrate main body part 411 by bending or folding the reinforcing plate 45 as much as the thickness of the substrate main body part 411 to form a step.

It should be noted that in the case in which the evaluating ultrasonic transducers 51T are not provided with the opening parts disposed in the substrate main body part 411 as in the case of the second embodiment, since the evaluation element region reinforcing parts 452 can directly be disposed on the extending parts 412B, 412C, a flat plate having a frame-like shape can be used as the reinforcing plate 45.

Further, similarly in the third embodiment, it is also possible to dispose the opening parts in the areas overlapping the extending parts 412B, 412C of the substrate main body part 411, and to configure the evaluating ultrasonic transducers 51T each including the vibrating part, the piezoelectric element, the electrode, and the opening part. It should be noted that also in this case, in the third embodiment, a flat plate having a frame-like shape can be used as the reinforcing plate 45.

Although in each of the embodiments described above, the surface (the reinforcing plate surface) on the +Z side of the reinforcing plate 45 is located on the +Z side with respect to the opening surfaces in the opening parts 411A, the invention is not limited to this configuration. Specifically, the reinforcing plate surface can also be located on the same plane, or on the −Z side with respect to the opening surfaces described above. It should be noted that in the case in which the reinforcing plate surface is coplanar with the opening surfaces described above, it becomes possible to form the acoustic matching layer 43 having the uniform thickness dimension with reference to the reinforcing plate surface similarly to each of the embodiments described above.

Although in the third embodiment described above, the inter-element region reinforcing parts 453 of the reinforcing plate 45 cover the partition wall parts 411B in the direction along the X direction out of the partition wall parts 411B of the substrate main body part 411, the invention is not limited to this configuration. Specifically, the inter-element region reinforcing parts 453 can also be formed to cover the partition wall parts 411B in a direction along the Y direction. Further, it is also possible to form the inter-element region reinforcing parts 453 to have a grid shape so as to cover the partition wall parts 411B in the direction along the X direction and the partition wall parts 411B in the direction along the Y direction.

It should be noted that since it is possible to inhibit the ultrasonic transducer array 50 from bending along the Y direction as the scanning direction by forming the inter-element region reinforcing parts 453 so as to cover the partition wall parts 411B in the direction along the Y direction, the directions of the ultrasonic waves emitted can be uniformed in a predetermined direction between the ultrasonic transducer groups 51A. Further, it is also possible to reduce the cross talk between the ultrasonic transducers 51 arranged in the X direction.

Further, although in the third embodiment described above, the terminal region reinforcing parts 451 and the evaluation element region reinforcing parts 452 of the reinforcing plate 45 are disposed in the substrate main body part 411, the invention is not limited to this configuration. It is also possible to adopt a configuration in which, for example, the extending parts 412B, 412C, 412D, and 412E are exposed from the substrate main body part 411, and the terminal region reinforcing parts 451 and the evaluation element region reinforcing parts 452 are directly disposed on the extending parts 412B, 412C, 412D, and 412E. In this case, there is adopted a configuration in which the inter-element region reinforcing parts 453 are each formed of a separated member from the terminal region reinforcing parts 451 and the evaluation element region reinforcing parts 452, and are disposed on the substrate main body part 411. Alternatively, it is also possible to adopt a configuration in which the inter-element region reinforcing parts 453 run on the substrate main body part 411 by bending or folding the reinforcing plate 45 to form a step.

Although in each of the embodiments described above, 42-alloy is cited as an example of the material of the reinforcing plate 45, the invention is not limited to this example. For example, by using a material (e.g., titanium) relatively low in thermal conductivity as the material of the reinforcing plate 45, it becomes difficult for the heat to be conducted to the protective member 47 when mounting, and therefore, the stress applied to the element substrate can be reduced.

Although in each of the embodiments described above, the ultrasonic device is mounted on the wiring board 23 using the FPC 46, the invention is not limited to this configuration. It is also possible to mount the ultrasonic device on the wiring board 23 by, for example, providing through electrodes penetrating the sealing plate 42 in the thickness direction to the sealing plate 42, connecting end parts in the +Z direction of the through electrodes to the respective electrode pads 414P, 416P of the element substrate, and connecting end parts in the −Z direction to the wiring terminal parts 231 of the wiring board 23. Although in this case, there is also the possibility that the stress is applied to the vicinity of each of the electrode pads 414P, 416P of the element substrate when mounting, since in each of the embodiments described above, the reinforcing plate 45 is disposed in the position overlapping the electrode pads 414P, 416P in the planar view in the element substrate, the warp of the element substrate can be suppressed.

Although in each of the embodiments described above, there is adopted the configuration in which the opening parts 411A are disposed in the element substrate, it is also possible to adopt a configuration in which, for example, the opening parts 411A are not disposed in the element substrate, the ultrasonic transducers 51 each vibrate the element substrate itself to emit the ultrasonic wave, and detect the reception of the ultrasonic wave based on the vibration of the element substrate.

Further, although there is illustrated the configuration of disposing the vibrating parts 412A on the −Z side of the opening parts 411A, it is also possible to adopt a configuration in which, for example, the vibrating part is disposed on the +Z side of the opening part 411A, and the piezoelectric element constituting the ultrasonic transducer 51 is disposed on the −Z side of the vibrating part.

Although in each of the embodiments described above, there is adopted the configuration in which the vibrating film 412 is disposed on the −Z side of the substrate main body part 411 provided with the opening parts 411A, the invention is not limited to this configuration. It is also possible to adopt a configuration in which, for example, a plurality of concave grooves corresponding respectively to the ultrasonic transducers 51 is disposed on the +Z side of the substrate main body part 411, and the bottom surface of each of the concave grooves is used as the vibrating film.

Although in each of the embodiments described above, there is described the example in which the piezoelectric element is formed of the laminated body having the lower-part electrode, the piezoelectric film, and the upper-part electrode stacked in the thickness direction, the invention is not limited to this example. It is also possible to adopt a configuration in which, for example, a pair of electrodes are disposed on one surface perpendicular to the thickness direction of the piezoelectric film so as to be opposed to each other. Further, it is also possible to dispose the electrodes on the side surfaces along the thickness direction of the piezoelectric film so as to sandwich the piezoelectric film.

Although in each of the embodiments described above, there is described the configuration for measuring the internal tomographic structure of a living body as an example of the ultrasonic measurement apparatus, the invention can also be used as other devices such as a measuring instrument for inspecting the internal structure of a concrete such as a concrete building.

Further, although the ultrasonic measurement apparatus provided with the ultrasonic device is illustrated, the invention can also be applied to other electronic apparatuses. The invention can be used for an ultrasonic washing machine for feeding the ultrasonic wave to a cleansing object to perform ultrasonic cleansing on the cleansing object.

Figure 11:
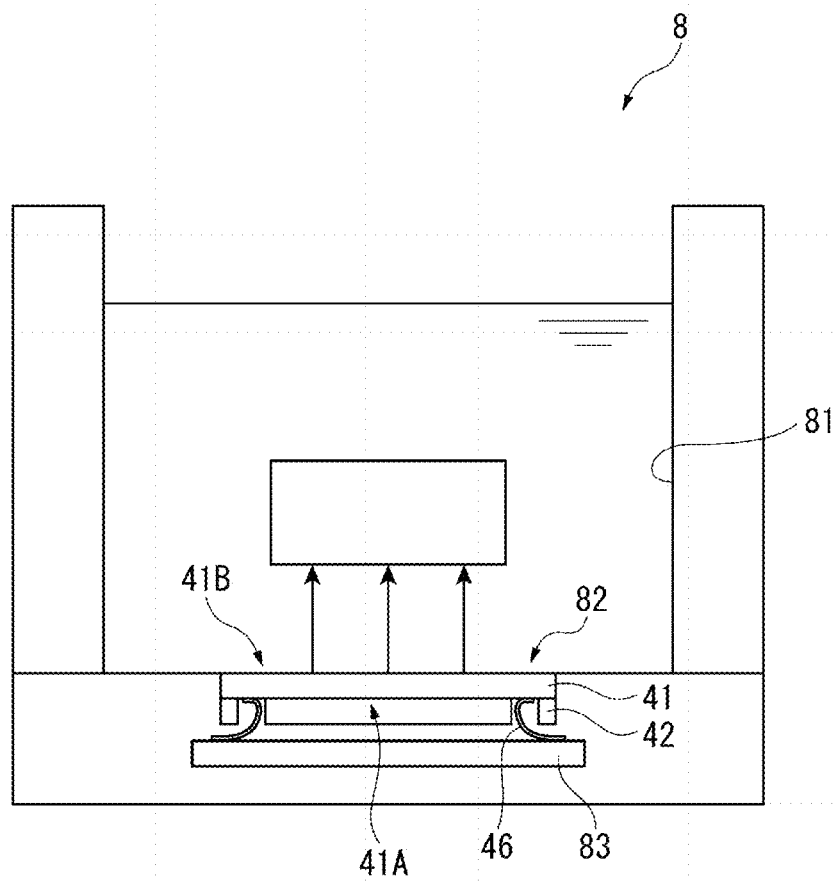
FIG. 11 is a diagram showing an example of an electronic apparatus according to another embodiment of the invention.

FIG. 11 is a diagram showing a general configuration of the ultrasonic washing machine.

The ultrasonic washing machine 8 shown in FIG. 11 is provided with a washing tank 81, and an ultrasonic module 82 disposed on, for example, a bottom surface of the washing tank 81.

The ultrasonic module 82 is provided with the ultrasonic device 22 substantially the same as that of each of the embodiments described above, and a wiring board 83 for controlling the ultrasonic device 22. Specifically, the ultrasonic device 22 is provided with the element substrate 41 having an operation surface 41B facing the inner surface of the washing tank 81, and the sealing plate 42 disposed on the rear surface 41A of the element substrate 41, and is provided with the ultrasonic transducer array 50 (not shown in FIG. 11) constituted by the plurality of ultrasonic transducers 51 (not shown in FIG. 11), and electrode lines drawn to the outside of the array region Ar1 (not shown in FIG. 11) of the ultrasonic transducer array 50 on the rear surface 41A side of the element substrate 41. Further, the electrode lines are connected to the electrodes of the FPC 46 inserted in the through hole 422 of the sealing plate 42 in the terminal region Ar2 outside the array region Ar1 to thereby be electrically connected to the wiring terminal parts (not shown) provided to the wiring board 83 via the FPC 46.

In such a configuration, the ultrasonic device 22 can easily be mounted on the wiring board 83 using face-down mounting. Further, since the operation surface 41B side of the element substrate 41 faces the washing tank 81 side, the waterproof property of the ultrasonic transducers 51 and the electrode lines disposed on the rear surface 41A side can be enhanced.

Besides the above, specific structures to be adopted when implementing the invention can be configured by arbitrarily combining the embodiments and the modified examples described above, or can arbitrarily be replaced with other structures and so on within the range in which the advantages of the invention can be achieved.

The entire disclosure of Japanese Patent Application No. 2015-150418 filed on Jul. 30, 2015 is expressly incorporated by reference herein.

What is claimed is:

1. An ultrasonic device comprising:
an element substrate having first and second surfaces opposite to each other;
an ultrasonic transducer array that is disposed on the first surface of the element substrate, the ultrasonic transducer array being configured with a plurality of ultrasonic transducers;
at least one terminal disposed on the first surface of the element substrate, the at least one terminal being located at an outside of the ultrasonic transducer array in a plan view, the at least one terminal being electrically connected to the plurality of ultrasonic transducers; and
a reinforcing plate that is disposed on the second surface of the element substrate, the reinforcing plate being overlapped with the at least one terminal in the plan view, bending rigidity of the reinforcing plate is higher than bending rigidity of the element substrate,
wherein the reinforcing plate is not overlapped with the plurality of ultrasonic transducers in the plan view,
the reinforcing plate is in a frame-like shape, and the reinforcing plate surrounds the ultrasonic transducer array in the plan view,
the ultrasonic transducer array has a plurality of ultrasonic transducer groups, each of the plurality of ultrasonic transducer groups has the plurality of ultrasonic transducers arranged along a first direction and connected to each other by a same signal line, and the plurality of ultrasonic transducer groups is arranged along a second direction crossing the first direction,
the element substrate is provided with a plurality of evaluating ultrasonic transducers arranged along the first direction and disposed on both sides in the second direction of the ultrasonic transducer array,
the at least one terminal is disposed on both ends in the first direction of each of the plurality of ultrasonic transducer groups, and
the reinforcing plate is configured with a terminal region reinforcing part and an evaluation element region reinforcing part, the terminal region reinforcing part is disposed along the second direction on both ends in the first direction of the ultrasonic transducer array, and the evaluation element region reinforcing part is disposed along the first direction on both ends in the second direction of the ultrasonic transducer array, and
the evaluation element region reinforcing part is overlapped with the plurality of evaluating ultrasonic transducers in the plan view.

* * * * *